(12) United States Patent
Fisher et al.

(10) Patent No.: US 6,858,714 B2
(45) Date of Patent: Feb. 22, 2005

(54) CYCLIC GMP PHOSPHODIESTERASE

(75) Inventors: Douglas A. Fisher, Groton, CT (US); Douglas H. Gooding, Redwood City, CA (US); David Gray Streeter, Boulder Creek, CA (US)

(73) Assignee: Incyte Corporation, Palo Alto, CA (US)

( * ) Notice: Subject to any disclaimer, the term of this patent is extended or adjusted under 35 U.S.C. 154(b) by 104 days.

(21) Appl. No.: 09/802,741

(22) Filed: Mar. 8, 2001

(65) Prior Publication Data

US 2002/0007046 A1 Jan. 17, 2002

Related U.S. Application Data

(62) Division of application No. 09/240,359, filed on Jan. 29, 1999, now Pat. No. 6,255,456, which is a division of application No. 08/987,466, filed on Dec. 9, 1997, now Pat. No. 5,922,595.

(51) Int. Cl.[7] .............................................. C07H 21/02
(52) U.S. Cl. ..................... 536/23.1; 536/23.5; 530/350; 435/69.1; 435/71.1; 435/320.1; 435/6
(58) Field of Search .............................. 536/23.1, 23.5; 530/350; 435/69.1, 71.1, 320.1, 6

(56) References Cited

U.S. PATENT DOCUMENTS 5,922,595 A * 7/1999 Ficher et al. ............ 435/320.1

FOREIGN PATENT DOCUMENTS

WO    WO 97 35989    10/1997

OTHER PUBLICATIONS

Database EST Accession No. AA502909 (8/97).*
Database EST Accession No. AA535891 (8/97).*
Skolnick et al TIBTECH vol. 18 p. 34 (1/00).*
Beavo, J.A., "Cyclic Nucleotide Phosphodiesterases: Functional Implications of Multiple Isoforms", *Physiological Reviews*, 75: 725–748 (1995).
Verghese, M.W. et al., "Regulation of Distinct Cyclic AMP–Specific Phosphodiesterase (Phosphodiesterase Type 4) Isozymes in Human Monocytic Cells", *Mol. Pharmacol.*, 47: 1164–1171 (1995).
Angel, J.B. et al., "Rolipram, a specific type IV phosphodiesterase inhibitor, is a potent inhibitor of HIV–1 replication", *AIDS*, 9: 1137–1144 (1995).
Sommer, N. et al., "The antidepressant rolipram suppresses cytokine production and prevents autoimmune encephalomyelitis", *Nat. Med.*, 1: 244–248 (1995).

Sasaki, H. et al., "Suppression of oro–facial movements by rolipram, a cAMP phosphodiesterase inhibitor, in rats chronically treated with haloperido", *Eur. J. Pharmacol.*, 282: 71–76 (1995).
Banner, K.H. and C.P. Page, "Theophylline and selective phosphodiesterase inhibitors as anti–inflammatory drugs in the treatment of bronchial asthma", *Eur. Respir. J.*, 8: 996–1000 (1995).
Bang, Y.–J. et al., "Terminal neuroendocrine differentiation of human prostate carcinoma cells in response to increased intracellular cyclic AMP", *Proc. Natl. Acad. Sci. USA*, 91: 5330–5334 (1994).
Matousovic, K. et al., "Inhibitors of Cyclic Nucleotide Phosphodiesterase Isozymes Type–III and Type–IV Suppress Mitogenesis of Rat Mesangial Cells", *J. Clin. Invest.*, 96: 401–410 (1995).
Joulain, C. et al., "Influence of polyunsaturated fatty acids on lipid metabolism in human blood mononuclear cells and early biochemical events associated with lymphocyte activation", *J. Lipid Mediat. Cell Signal.*, 11: 63–79 (1995).
Deonarain M.P. and A. Epenetos, "Targeting enzymes for cancer therapy: old enzymes in new roles", *Br. J. Cancer*, 70: 786–794 (1994).
Davis, R. and Y. Qiu, (Direct Submission), GenBank Sequence Database (Accession X55167, S70588, S70600, X55247), National Center for Biotechnology Information, National Library of Medicine, Bethesda, Maryland, 20894 (GI 7897; GI 829179), 1993.
Qiu, Y. et al., "Characterization of the Memory Gene Dunce of *Drosophila melanogaster*", *J. Mol. Biol.*, 222: 553–565 (1991), (GI 7897; GI 829179).
Segel, I.H., *Enzyme Kinetics*, John Wiley and Sons, New York, NY, pp. 214–245 (1995).
National Cancer Institute, Cancer Genome Anatomy Project: "*Homo sapiens* cDNA clone IMAGE:900018 similar to WP:R153.1 CE02038 Cyclic Nucleotide Phosphodiesterase," (Acc. No. AA502909) (GI 2237876), Jul. 4, 1997.
Fisher, D.A. et al., "Isolation and Characterization of PDE9A, a Novel Human cGMP–specific Phosphodiesterase," *J. Biol. Chem.*, 273(25):15559–15564 (1998).

* cited by examiner

*Primary Examiner*—Sheela J. Huff
(74) *Attorney, Agent, or Firm*—Foley & Lardner LLP

(57) ABSTRACT

The invention provides a human cyclic GMP phosphodiesterase (PDE9A) and polynucleotides which identify and encode PDE9A. The invention also provides expression vectors, host cells, antibodies, agonists, and antagonists. The invention also provides methods for treating or preventing disorders associated with expression of PDE9A.

12 Claims, 13 Drawing Sheets

```
                                9            18           27           36           45           54
5' GCT CCC CGC GGC GGC TGG CGT CGG GAA AGT ACA GTA AAA AGT CCG AGT GCA GCC 63           72           81           90           99          108
   GCC GGG CGC AGG ATG GGA TCC GGC ATT CAG CGC ATT TTC AGC CCC AAG GCC ATC TAC
                           M   G   S   G   I   Q   R   I   F   S   P   K   A   I   Y 117          126          135          144          153          162
   CTG GAC ATC GAT GGA CGC ATT CAG AAG GTA ATC TTC AGC AAG TAC TGC AAC TCC
    L   D   I   D   G   R   I   Q   K   V   I   F   S   K   Y   C   N   S 171          180          189          198          207          216
   AGC GAC ATC ATG GAC CTG TTC TGC ATC GCC ACC GGC CTG CCT CGG AAC ACG ACC
    S   D   I   M   D   L   F   C   I   A   T   G   L   P   R   N   T   T 225          234          243          252          261          270
   ATC TCC CTG CTG ACC ACC GAC GAC GCC ATG GTC TCC ATC GAC CCC ACC ATG CCC
    I   S   L   L   T   T   D   D   A   M   V   S   I   D   P   T   M   P 279          288          297          306          315          324
   GCG AAT TCA GAA CGC ACT CCG TAC AAA GTG AGA CCT GTG GCC ATC AAG CAA CTC
    A   N   S   E   R   T   P   Y   K   V   R   P   V   A   I   K   Q   L 333          342          351          360          369          378
   TCC GGT GGT GTC GAG GAC AAG AGA ACC ACA AGC CGT GGC CAG TCT GCT GAG AGA
    S   G   G   V   E   D   K   R   T   T   S   R   G   Q   S   A   E   R
```

FIGURE 1A

```
         387              396       405              414       423              432
CCA CTG AGG GAC AGA CGG GTT GTG GGC CTG GAG CAG CCC CGG AGG GAA GGA GCA
 P   L   R   D   R   R   V   V   G   L   E   Q   P   R   R   E   G   A 441              450       459              468       477              486
TTT GAA AGT GGA CAG GTA GAG CCC AGG CCC AGA GAG CCC CAG GGC TGC TAC CAG
 F   E   S   G   Q   V   E   P   R   P   R   E   P   Q   G   C   Y   Q 495              504       513              522       531              540
GAA GGC CAG CGC ATC CCT CCA GAG AGA GAA GAA TTA ATC CAG AGC GTG CTG GCG
 E   G   Q   R   I   P   P   E   R   E   E   L   I   Q   S   V   L   A 549              558       567              576       585              594
CAG GTT GCA GAG CAG CAG TTC TCA AGA GCA TTC AAA ATC AAT GAA CTG AAA GCT GAA
 Q   V   A   E   Q   Q   F   S   R   A   F   K   I   N   E   L   K   A   E 603              612       621              630       639              648
GTT GCA AAT CAC TTG GCT GTC CTA GAG AAA CGC GTG GAA TTG GAA GGA CTA AAA
 V   A   N   H   L   A   V   L   E   K   R   V   E   L   E   G   L   K 657              666       675              684       693              702
GTG GTG GAG ATT GAG AAA TGC AAG AGT GAC ATT AAG AAG ATG AGG GAG GAG CTG
 V   V   E   I   E   K   C   K   S   D   I   K   K   M   R   E   E   L 711              720       729              738       747              756
GCG GCC AGA AGC AGC AGG ACC AAC AGG ACC AAC TGC CCC TGT AAG TAC AGT TTT TTG GAT AAC
 A   A   R   S   S   R   T   N   R   T   N   C   P   C   K   Y   S   F   L   D   N
```

FIGURE 1B

```
      765           774           783           792           801           810
CAC AAG AAG TTG ACT CCT CGA CGC GAT GTT CCC ACT TAC CCC AAG TAC CTG CTC
 H   K   K   L   T   P   R   R   D   V   P   T   Y   P   K   Y   L   L 819           828           837           846           855           864
TCT CCA GAG ACC ATC GAG GCC CTG CGG AAG CCG ACC TTT GAC GTC TGG CTT TGG
 S   P   E   T   I   E   A   L   R   K   P   T   F   D   V   W   L   W 873           882           891           900           909           918
GAG CCC AAT GAG ATG CTG AGC TGC CTG GAG CAC ATG TAC CAC GAC CTC GGG CTG
 E   P   N   E   M   L   S   C   L   E   H   M   Y   H   D   L   G   L 927           936           945           954           963           972
GTC AGG GAC TTC AGC ATC AAC CCT GTC ACC CTC ACC AGG AGG TGG CTG TTC TGT GTC
 V   R   D   F   S   I   N   P   V   T   L   T   R   R   W   L   F   C   V 981           990           999           1008          1017          1026
CAC GAC AAC TAC AGA AAC AAC CCC TTC CAC AAC TTC CGG CAC TGC TTC TGC GTG
 H   D   N   Y   R   N   N   P   F   H   N   F   R   H   C   F   C   V 1035          1044          1053          1062          1071          1080
GCC CAG ATG ATG TAC AGC ATG GTC TGG CTC TGC AGT CTC TGC CAG GAG AAG TTC TCA
 A   Q   M   M   Y   S   M   V   W   L   C   S   L   C   Q   E   K   F   S 1089          1098          1107          1116          1125          1134
CAA ACG GAT ATC CTG ATC CTA ATG ACA GCG GCC ATC TGC CAC GAT CTG GAC CAT
 Q   T   D   I   L   I   L   M   T   A   A   I   C   H   D   L   D   H
```

FIGURE 1C

```
       1143              1152              1161              1170              1179              1188
CCC GGC TAC AAC AAC ACG TAC CAG ATC AAT GCC CGC ACA GAG CTG GCG GTC CGC
 P   G   Y   N   N   T   Y   Q   I   N   A   R   T   E   L   A   V   R 1197              1206              1215              1224              1233              1242
TAC AAT GAC ATC TCA CCG CTG GAG AAC CAC CAC TGC GCC GTG GCC TTC CAG ATC
 Y   N   D   I   S   P   L   E   N   H   H   C   A   V   A   F   Q   I 1251              1260              1269              1278              1287              1296
CTC GCC GAG CCT GAG TGC AAC ATC TTC TCC AAC ATC CCA CCT GAT GGG TTC AAG
 L   A   E   P   E   C   N   I   F   S   N   I   P   P   D   G   F   K 1305              1314              1323              1332              1341              1350
CAG ATC CGA CAG GGA ATG ATC ACA TTA ATC TTG GCC ACT GAC ATG GCA AGA CAT
 Q   I   R   Q   G   M   I   T   L   I   L   A   T   D   M   A   R   H 1359              1368              1377              1386              1395              1404
GCA GAA ATT ATG GAT TCT TTC AAA GAG AAA ATG GAG AAT TTT GAC TAC AGC AAC
 A   E   I   M   D   S   F   K   E   K   M   E   N   F   D   Y   S   N 1413              1422              1431              1440              1449              1458
GAG CAC ATG ACC CTG AAG CTG AAG ATG ATT TTG ATA AAA TGC TGT GAT ATC TCT
 E   H   M   T   L   K   L   K   M   I   L   I   K   C   C   D   I   S 1467              1476              1485              1494              1503              1512
GAG GAG GTC CCA ATG GAA GTC GCA GAG CCT TGG GTG GAC TGT TTA TTA GAG
 E   E   V   P   M   E   V   A   E   P   W   V   D   C   L   L   E 1467              1476              1485              1494              1503              1512
AAC GAG GTC CGT CCA ATG GAA GTC GCA GAG CCT TGG GTG GAC TGT TTA TTA GAG
 N   E   V   R   P   M   E   V   A   E   P   W   V   D   C   L   L   E
```

FIGURE 1D

```
      1521           1530           1539           1548           1557           1566
GAA TAT TTT ATG CAG AGC GAC CGT GAG AAG TCA GAA GGC CTT CCT GTG GCA CCG
 E   Y   F   M   Q   S   D   R   E   K   S   E   G   L   P   V   A   P 1575           1584           1593           1602           1611           1620
TTC ATG GAC CGA GAC AAA GTG ACC AAG GCC ACA GCC CAG ATT GGG TTC ATC AAG
 F   M   D   R   D   K   V   T   K   A   T   A   Q   I   G   F   I   K 1629           1638           1647           1656           1665           1674
TTT GTC CTG ATC CCA ATG TTT GAA ACA GTG ACC AAG CTC TTC CCC ATG GTT GAG
 F   V   L   I   P   M   F   E   T   V   T   K   L   F   P   M   V   E 1683           1692           1701           1710           1719           1728
GAG ATC ATG CTG CAG CCA CTT TGG GAA TCC CGA GAT CGC TAC GAG GAG CTG AAG
 E   I   M   L   Q   P   L   W   E   S   R   D   R   Y   E   E   L   K 1737           1746           1755           1764           1773           1782
CGG ATA GAT GAC GCC ATG AAA GAG TTA CAG AAG AAG ACT GAC AGC TTG ACG TCT
 R   I   D   D   A   M   K   E   L   Q   K   K   T   D   S   L   T   S 1791           1800           1809           1818           1827           1836
GGG GCC GAG AAG ACC AGA TCC AGA GAG AGC AGA GAT GTG AAA AAC AGT GAA GGA
 G   A   E   K   T   R   S   R   E   S   R   D   V   K   N   S   E   G 1845           1854           1863           1872           1881           1890
GAC TGT GCC TGA GGA AAG CGG GGG GCG TGG CTG CAG TTC TGG ACG GGC TGG CCG
 D   C   A   *
```

FIGURE 1E

```
       1899      1908      1917      1926      1935      1944
AGC TGC GCG GGA TCC TTG TGC AGG GAA GAG CTG CCC TGG GCA CCT GGC ACC ACA 1953      1962      1971      1980      1989
AGA CCA TGT TTT CTA AGA ACC ATT TTG TTC ACT GAT ACA AAA AAA AAA AAA AA 3'
```

```
118 RREGAFESGQV------------------------EPRPREPQGCYQEGQRIP PDE9A
200 IRHY-VSIIRVCNGNNKAEKISECVQSDTRTDNQTGKHKD              PDE8A
103 QQEFDLPSLRV---------EDNPELVAANAAAGQQSAGQYA            g829179

147 PEREEL-IQSVLAQVAE-----------------QFSRAFKINELKAE--VA  PDE9A
239 RRKGSLDVKAVASRATEVSSQRRHSMARIHSMTIEAPIT               PDE8A
136 RSRSP-------------RGPPMSQISGVK-                       g829179

179 NHLAVLEKRVE------------------LEGLKVVEIEKCKSDI         PDE9A
279 KVINVINAAQESSPMPVTEALDRVLEILRTTELYSPQFGA              PDE8A
153 ------RPLSHTNSFT-----GERL--PTFGV                      g829179

206 KK------MREELAARSSRTNCPCKYSFLDNHKKLTPRR               PDE9A
319 KDDDPHANDLVGGLMSDGLRRLSGNEYVLSTKNTQMVSSN              PDE8A
172 --ETPRENEL-GTLLGE---                                  g829179

239 DVPTYPKYLLSPETIEALRKPTFDVWLWEPNEM-----                PDE9A
359 ITPISLDDVPPRIARAMENEEY---WDFDIFELEAATHNR              PDE8A
186 ----LDT----------------WGIQIFSIGEFSVNR                g829179
```

FIGURE 2B

```
272  -LSCLE-HMYHDLGLVRDFSINPVTLRRWLFCVHDNY--RN   PDE9A
397  PLIYLGLKMFARFGICEFLHCSESTLRSWLQIIEANYHSS    PDE8A
204  PLTCVAYTIFQSRELLTSLMIPPKTFLNFMSTLEDHYVKD    g829179

309  NPFHNFRHCFCVAQMMYSMVWLCSLQEKFSQTDILILMTA    PDE9A
437  NPYHNSTHSADVLHATAYFLSKERIKETLDPIDEVAALIA    PDE8A
244  NPFHNSLHAADVTQSTNVLLNTPALEGVFTPLEVGGALFA    g829179

349  AICHDLDHPGYNNTYQINARTELAVRYNDISPLENHHCAV    PDE9A
477  ATIHDVDHPGRTNSFLCNAGSELAILYNDTAVLESHHAAL    PDE8A
284  ACIHDVDHPGLTNQFLVNSSSELALMYNDESVLENHHLAV    g829179

389  AFQILAEPE-CNIFSNIPPDGFKQIRQGMITLILATDMAR    PDE9A
517  AFQLTTGDDDKCNIFKNMERNDYRTLRQGIIDMVLATEMTK   PDE8A
324  AFKLLQNQG-CDIFCNMQKKQRQTLRKMVIDIVLSTDMSK    g829179

428  HAEIMDSF---KEKMENFDYSNE-----E              PDE9A
557  HFEHVNKFVNSINKPLATLEENGETDKNQEVINTMLRTPE   PDE8A
363  HMSL------LADLKTMVETKKVAGSGVLLLDNYT        g829179
```

FIGURE 2C

```
449 H M T L L K M I L I K C C D I S N E V R P M E V A E P W V D C L L E E Y F M Q S   PDE9A
597 N R T L I K R M L I K C A D V S N P C R P L Q Y C I E W A A R I S E E Y F S Q T   PDE8A
392 D R I Q V L E N L V H C A D L S N P T K P L P L Y K R W V A L L M E E F L Q G   g829179

489 D R E K S E G L P V A - P F M D R D K V T K A T A Q I G F I K F V L I P M F E T   PDE9A
637 D E E K Q Q G L P V V M P V F D R N T C S I P K S Q I S F I D Y F I T D M F D A   PDE8A
432 D K E R E S G M D I S - P M C D R H N A T I E K S Q V G F I D Y I V H P L W E T   g829179

528 V T K L F P M V E E I M L Q P L - - - - - W - - - - - - - - - - - - - T S G A   PDE9A
677 W D A F V - - D L P D L M Q H L D N N F K Y W K G L - - - - - - - - - - - - -   PDE8A
471 W A S L V H P D A Q D I L D T L E E N R D Y Y Q S M I P P S P P P S G V D E N P   g829179

545 - E S R D R Y E - E L K R I D D A - M K E L Q K K T D S L - - - - - - - - - -   PDE9A
701 - - - - - - - - - - - - - - - - - D E M K L R N L R P P P E                     PDE8A
511 Q E D R I R F Q V T L E E S D Q E N L A E L E E G D E S G G E T T T T G T T G T   g829179

575 T E K S R E R S R D - - - - - - - V K N S E G D C A                             PDE9A
713                                                                                 PDE8A
551 T A A S A L R A G G G G G G M A P R T G G C Q N Q P Q H G G M                   g829179
```

FIGURE 2D

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
    (A) LENGTH: 593 amino acids
    (B) TYPE: amino acid
    (C) STRANDEDNESS: single
    (D) TOPOLOGY: linear (vii) IMMEDIATE SOURCE:
    (A) LIBRARY: PROSNOT06
    (B) CLONE: 828228

(xi) SEQUENCE DESCRIPTION: SEQ ID NO: 1:

```
Met Gly Ser Gly Ser Ser Ser Tyr Arg Pro Lys Ala Ile Tyr Leu Asp
 1               5                  10                  15

Ile Asp Gly Arg Ile Gln Lys Val Ile Phe Ser Lys Tyr Cys Asn Ser
            20                  25                  30

Ser Asp Ile Met Asp Leu Phe Cys Ile Ala Thr Gly Leu Pro Arg Asn
        35                  40                  45

Thr Thr Ile Ser Leu Leu Thr Thr Asp Ala Met Val Ser Ile Asp
 50                  55                  60

Pro Thr Met Pro Ala Asn Ser Glu Arg Thr Pro Tyr Lys Val Arg Pro
 65                  70                  75                  80

Val Ala Ile Lys Gln Leu Ser Ala Gly Val Glu Asp Lys Arg Thr Thr
                85                  90                  95

Ser Arg Gly Gln Ser Ala Glu Arg Pro Leu Arg Asp Arg Arg Val Val
            100                 105                 110

Gly Leu Glu Gln Pro Arg Arg Glu Gly Ala Phe Glu Ser Gly Gln Val
        115                 120                 125

Glu Pro Arg Pro Arg Glu Pro Gln Gly Cys Tyr Gln Glu Gly Gln Arg
130                 135                 140

Ile Pro Pro Glu Arg Glu Glu Leu Ile Gln Ser Val Leu Ala Gln Val
145                 150                 155                 160

Ala Glu Gln Phe Ser Arg Ala Phe Lys Ile Asn Glu Leu Lys Ala Glu
                165                 170                 175

Val Ala Asn His Leu Ala Val Leu Glu Lys Arg Val Glu Leu Glu Gly
            180                 185                 190

Leu Lys Val Val Glu Ile Glu Lys Cys Lys Ser Asp Ile Lys Lys Met
        195                 200                 205

Arg Glu Glu Leu Ala Ala Arg Ser Ser Arg Thr Asn Cys Pro Cys Lys
210                 215                 220

Tyr Ser Phe Leu Asp Asn His Lys Lys Leu Thr Pro Arg Arg Asp Val
225                 230                 235                 240

Pro Thr Tyr Pro Lys Tyr Leu Leu Ser Pro Glu Thr Ile Glu Ala Leu
                245                 250                 255

Arg Lys Pro Thr Phe Asp Val Trp Leu Trp Glu Pro Asn Glu Met Leu
            260                 265                 270

Ser Cys Leu Glu His Met Tyr His Asp Leu Gly Leu Val Arg Asp Phe
        275                 280                 285

Ser Ile Asn Pro Val Thr Leu Arg Arg Trp Leu Phe Cys Val His Asp
290                 295                 300
```

-continued

```
Asn Tyr Arg Asn Asn Pro Phe His Asn Phe Arg His Cys Phe Cys Val
305                 310                 315                 320

Ala Gln Met Met Tyr Ser Met Val Trp Leu Cys Ser Leu Gln Glu Lys
            325                 330                 335

Phe Ser Gln Thr Asp Ile Leu Ile Leu Met Thr Ala Ala Ile Cys His
            340                 345                 350

Asp Leu Asp His Pro Gly Tyr Asn Asn Thr Tyr Gln Ile Asn Ala Arg
            355                 360                 365

Thr Glu Leu Ala Val Arg Tyr Asn Asp Ile Ser Pro Leu Glu Asn His
        370                 375                 380

His Cys Ala Val Ala Phe Gln Ile Leu Ala Glu Pro Glu Cys Asn Ile
385                 390                 395                 400

Phe Ser Asn Ile Pro Pro Asp Gly Phe Lys Gln Ile Arg Gln Gly Met
                405                 410                 415

Ile Thr Leu Ile Leu Ala Thr Asp Met Ala Arg His Ala Glu Ile Met
            420                 425                 430

Asp Ser Phe Lys Glu Lys Met Glu Asn Phe Asp Tyr Ser Asn Glu Glu
            435                 440                 445

His Met Thr Leu Leu Lys Met Ile Leu Ile Lys Cys Cys Asp Ile Ser
        450                 455                 460

Asn Glu Val Arg Pro Met Glu Val Ala Glu Pro Trp Val Asp Cys Leu
465                 470                 475                 480

Leu Glu Glu Tyr Phe Met Gln Ser Asp Arg Glu Lys Ser Glu Gly Leu
                485                 490                 495

Pro Val Ala Pro Phe Met Asp Arg Asp Lys Val Thr Lys Ala Thr Ala
            500                 505                 510

Gln Ile Gly Phe Ile Lys Phe Val Leu Ile Pro Met Phe Glu Thr Val
            515                 520                 525

Thr Lys Leu Phe Pro Met Val Glu Glu Ile Met Leu Gln Pro Leu Trp
        530                 535                 540

Glu Ser Arg Asp Arg Tyr Glu Glu Leu Lys Arg Ile Asp Asp Ala Met
545                 550                 555                 560

Lys Glu Leu Gln Lys Lys Thr Asp Ser Leu Thr Ser Gly Ala Thr Glu
                565                 570                 575

Lys Ser Arg Glu Arg Ser Arg Asp Val Lys Asn Ser Glu Gly Asp Cys
            580                 585                 590

Ala
```

(2) INFORMATION FOR SEQ ID NO: 2:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (vii) IMMEDIATE SOURCE:
        (A) LIBRARY: PROSNOT06
        (B) CLONE: 828228

(xi) SEQUENCE DESCRIPTION: SEQ ID NO: 2:

```
GCTCCCCGCG GCGGCTGGCG TCGGGAAAGT ACAGTAAAAA GTCCGAGTGC AGCCGCCGGG      60

CGCAGGATGG GATCCGGCTC CTCCAGCTAC CGGCCCAAGG CCATCTACCT GGACATCGAT     120

GGACGCATTC AGAAGGTAAT CTTCAGCAAG TACTGCAACT CCAGCGACAT CATGGACCTG     180

TTCTGCATCG CCACCGGCCT GCCTCGGAAC ACGACCATCT CCCTGCTGAC CACCGACGAC     240
```

```
GCCATGGTCT CCATCGACCC CACCATGCCC GCGAATTCAG AACGCACTCC GTACAAAGTG      300
AGACCTGTGG CCATCAAGCA ACTCTCCGCT GGTGTCGAGG ACAAGAGAAC CACAAGCCGT      360
GGCCAGTCTG CTGAGAGACC ACTGAGGGAC AGACGGGTTG TGGGCCTGGA GCAGCCCCGG      420
AGGGAAGGAG CATTTGAAAG TGGACAGGTA GAGCCCAGGC CCAGAGAGCC CCAGGGCTGC      480
TACCAGGAAG CCAGCGCAT  CCCTCCAGAG AGAGAAGAAT TAATCCAGAG CGTGCTGGCG      540
CAGGTTGCAG AGCAGTTCTC AAGAGCATTC AAAATCAATG AACTGAAAGC TGAAGTTGCA      600
AATCACTTGG CTGTCCTAGA GAAACGCGTG GAATTGGAAG GACTAAAAGT GGTGGAGATT      660
GAGAAATGCA AGAGTGACAT TAAGAAGATG AGGGAGGAGC TGGCGGCCAG AAGCAGCAGG      720
ACCAACTGCC CCTGTAAGTA CAGTTTTTTG GATAACCACA AGAAGTTGAC TCCTCGACGC      780
GATGTTCCCA CTTACCCCAA GTACCTGCTC TCTCCAGAGA CCATCGAGGC CCTGCGGAAG      840
CCGACCTTTG ACGTCTGGCT TTGGGAGCCC AATGAGATGC TGAGCTGCCT GGAGCACATG      900
TACCACGACC TCGGGCTGGT CAGGGACTTC AGCATCAACC CTGTCACCCT CAGGAGGTGG      960
CTGTTCTGTG TCCACGACAA CTACAGAAAC AACCCCTTCC ACAACTTCCG GCACTGCTTC     1020
TGCGTGGCCC AGATGATGTA CAGCATGGTC TGGCTCTGCA GTCTCCAGGA GAAGTTCTCA     1080
CAAACGGATA TCCTGATCCT AATGACAGCG GCCATCTGCC ACGATCTGGA CCATCCCGGC     1140
TACAACAACA CGTACCAGAT CAATGCCCGC ACAGAGCTGG CGGTCCGCTA CAATGACATC     1200
TCACCGCTGG AGAACCACCA CTGCGCCGTG GCCTTCCAGA TCCTCGCCGA GCCTGAGTGC     1260
AACATCTTCT CCAACATCCC ACCTGATGGG TTCAAGCAGA TCCGACAGGG AATGATCACA     1320
TTAATCTTGG CCACTGACAT GGCAAGACAT GCAGAAATTA TGGATTCTTT CAAAGAGAAA     1380
ATGGAGAATT TTGACTACAG CAACGAGGAG CACATGACCC TGCTGAAGAT GATTTTGATA     1440
AAATGCTGTG ATATCTCTAA CGAGGTCCGT CCAATGGAAG TCGCAGAGCC TTGGGTGGAC     1500
TGTTTATTAG AGGAATATTT TATGCAGAGC GACCGTGAGA AGTCAGAAGG CCTTCCTGTG     1560
GCACCGTTCA TGGACCGAGA CAAAGTGACC AAGGCCACAG CCCAGATTGG GTTCATCAAG     1620
TTTGTCCTGA TCCCAATGTT TGAAACAGTG ACCAAGCTCT TCCCCATGGT TGAGGAGATC     1680
ATGCTGCAGC CACTTTGGGA ATCCCGAGAT CGCTACGAGG AGCTGAAGCG GATAGATGAC     1740
GCCATGAAAG AGTTACAGAA GAAGACTGAC AGCTTGACGT CTGGGCCCAC CGAGAAGTCC     1800
AGAGAGAGAA GCAGAGATGT GAAAAACAGT GAAGGAGACT GTGCCTGAGG AAAGCGGGGG     1860
GCGTGGCTGC AGTTCTGGAC GGGCTGGCCG AGCTGCGCGG GATCCTTGTG CAGGGAAGAG     1920
CTGCCCTGGG CACCTGGCAC CACAAGACCA TGTTTTCTAA GAACCATTTT GTTCACTGAT     1980
ACAAAAAAAA AAAAAAA                                                    1997
```

(2) INFORMATION FOR SEQ ID NO: 3:

(i) SEQUENCE CHARACTERISTICS:
        (A) LENGTH: 713 amino acids
        (B) TYPE: amino acid
        (C) STRANDEDNESS: single
        (D) TOPOLOGY: linear (vii) IMMEDIATE SOURCE:
        (A) LIBRARY: THP1PLB02
        (B) CLONE: 156196

(xi) SEQUENCE DESCRIPTION: SEQ ID NO: 3:

```
Leu Ala Cys Phe Leu Asp Lys His His Asp Ile Ile Ile Ile Asp His
  1               5                  10                  15
```

-continued

```
Arg Asn Pro Arg Gln Leu Asp Ala Glu Ala Leu Cys Arg Ser Ile Arg
         20                  25                  30

Ser Ser Lys Leu Ser Glu Asn Thr Val Ile Val Gly Val Arg Arg
         35                  40                  45

Val Asp Arg Glu Glu Leu Ser Val Met Pro Phe Ile Ser Ala Gly Phe
 50                  55                  60

Thr Arg Arg Tyr Val Glu Asn Pro Asn Ile Met Ala Cys Tyr Asn Glu
 65                  70                  75                  80

Leu Leu Gln Leu Glu Phe Gly Glu Val Arg Ser Gln Leu Lys Leu Arg
                 85                  90                  95

Ala Cys Asn Ser Val Phe Thr Ala Leu Glu Asn Ser Glu Asp Ala Ile
            100                 105                 110

Glu Ile Thr Ser Glu Asp Arg Phe Ile Gln Tyr Ala Asn Pro Ala Phe
            115                 120                 125

Glu Thr Thr Met Gly Tyr Gln Ser Gly Glu Leu Ile Gly Lys Glu Leu
            130                 135                 140

Gly Glu Val Pro Ile Asn Glu Lys Lys Ala Asp Leu Leu Asp Thr Ile
145                 150                 155                 160

Asn Ser Cys Ile Arg Ile Gly Lys Glu Trp Gln Gly Ile Tyr Tyr Ala
                165                 170                 175

Lys Lys Lys Asn Gly Asp Asn Ile Gln Gln Asn Val Lys Ile Ile Pro
            180                 185                 190

Val Ile Gly Gln Gly Gly Lys Ile Arg His Tyr Val Ser Ile Ile Arg
            195                 200                 205

Val Cys Asn Gly Asn Asn Lys Ala Glu Lys Ile Ser Glu Cys Val Gln
            210                 215                 220

Ser Asp Thr Arg Thr Asp Asn Gln Thr Gly Lys His Lys Asp Arg Arg
225                 230                 235                 240

Lys Gly Ser Leu Asp Val Lys Ala Val Ala Ser Arg Ala Thr Glu Val
                245                 250                 255

Ser Ser Gln Arg Arg His Ser Ser Met Ala Arg Ile His Ser Met Thr
            260                 265                 270

Ile Glu Ala Pro Ile Thr Lys Val Ile Asn Val Ile Asn Ala Ala Gln
            275                 280                 285

Glu Ser Ser Pro Met Pro Val Thr Glu Ala Leu Asp Arg Val Leu Glu
            290                 295                 300

Ile Leu Arg Thr Thr Glu Leu Tyr Ser Pro Gln Phe Gly Ala Lys Asp
305                 310                 315                 320

Asp Asp Pro His Ala Asn Asp Leu Val Gly Gly Leu Met Ser Asp Gly
                325                 330                 335

Leu Arg Arg Leu Ser Gly Asn Glu Tyr Val Leu Ser Thr Lys Asn Thr
            340                 345                 350

Gln Met Val Ser Ser Asn Ile Ile Thr Pro Ile Ser Leu Asp Asp Val
            355                 360                 365

Pro Pro Arg Ile Ala Arg Ala Met Glu Asn Glu Glu Tyr Trp Asp Phe
            370                 375                 380

Asp Ile Phe Glu Leu Glu Ala Ala Thr His Asn Arg Pro Leu Ile Tyr
385                 390                 395                 400

Leu Gly Leu Lys Met Phe Ala Arg Phe Gly Ile Cys Glu Phe Leu His
                405                 410                 415

Cys Ser Glu Ser Thr Leu Arg Ser Trp Leu Gln Ile Ile Glu Ala Asn
            420                 425                 430
```

-continued

```
Tyr His Ser Ser Asn Pro Tyr His Asn Ser Thr His Ser Ala Asp Val
            435                 440                 445

Leu His Ala Thr Ala Tyr Phe Leu Ser Lys Glu Arg Ile Lys Glu Thr
    450                 455                 460

Leu Asp Pro Ile Asp Glu Val Ala Ala Leu Ile Ala Ala Thr Ile His
465                 470                 475                 480

Asp Val Asp His Pro Gly Arg Thr Asn Ser Phe Leu Cys Asn Ala Gly
                485                 490                 495

Ser Glu Leu Ala Ile Leu Tyr Asn Asp Thr Ala Val Leu Glu Ser His
            500                 505                 510

His Ala Ala Leu Ala Phe Gln Leu Thr Thr Gly Asp Asp Lys Cys Asn
        515                 520                 525

Ile Phe Lys Asn Met Glu Arg Asn Asp Tyr Arg Thr Leu Arg Gln Gly
    530                 535                 540

Ile Ile Asp Met Val Leu Ala Thr Glu Met Thr Lys His Phe Glu His
545                 550                 555                 560

Val Asn Lys Phe Val Asn Ser Ile Asn Lys Pro Leu Ala Thr Leu Glu
                565                 570                 575

Glu Asn Gly Glu Thr Asp Lys Asn Gln Glu Val Ile Asn Thr Met Leu
            580                 585                 590

Arg Thr Pro Glu Asn Arg Thr Leu Ile Lys Arg Met Leu Ile Lys Cys
        595                 600                 605

Ala Asp Val Ser Asn Pro Cys Arg Pro Leu Gln Tyr Cys Ile Glu Trp
    610                 615                 620

Ala Ala Arg Ile Ser Glu Glu Tyr Phe Ser Gln Thr Asp Glu Glu Lys
625                 630                 635                 640

Gln Gln Gly Leu Pro Val Val Met Pro Val Phe Asp Arg Asn Thr Cys
                645                 650                 655

Ser Ile Pro Lys Ser Gln Ile Ser Phe Ile Asp Tyr Phe Ile Thr Asp
            660                 665                 670

Met Phe Asp Ala Trp Asp Ala Phe Val Asp Leu Pro Asp Leu Met Gln
        675                 680                 685

His Leu Asp Asn Asn Phe Lys Tyr Trp Lys Gly Leu Asp Glu Met Lys
    690                 695                 700

Leu Arg Asn Leu Arg Pro Pro Glu
705                 710

(2) INFORMATION FOR SEQ ID NO: 4:

(i) SEQUENCE CHARACTERISTICS:
        (A) LENGTH: 584 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 829179

(xi) SEQUENCE DESCRIPTION: SEQ ID NO: 4:

Met Phe Gln His Gln Thr Asn Pro Gly Gly Pro Thr Asn Arg Arg Arg
1               5                   10                  15

Pro Arg Asp Gln Glu Ile His Gln Glu Pro Arg Tyr Pro Lys Ala Arg
            20                  25                  30

Arg His Thr Pro Ala Trp Pro Thr Gln Ser Arg Ser Trp Thr Gly
        35                  40                  45
```

-continued

```
Ala Ser Thr Ser Trp Arg Pro Ser Arg Pro Ile Ala Ala Ser Pro Thr
 50                  55                  60

Trp Arg Arg Leu Ser Ser Asn Ala Cys Ser Thr Arg Ser Cys Arg Thr
 65                  70                  75                  80

Leu Ala Ser Pro Ala Asp Arg Glu Ile Arg Phe Pro Asn Ile Tyr Val
                 85                  90                  95

Pro His Phe Trp Asp Lys Gln Gln Glu Phe Asp Leu Pro Ser Leu Arg
            100                 105                 110

Val Glu Asp Asn Pro Glu Leu Val Ala Ala Asn Ala Ala Ala Gly Gln
        115                 120                 125

Gln Ser Ala Gly Gln Tyr Ala Arg Ser Arg Ser Pro Arg Gly Pro Pro
    130                 135                 140

Met Ser Gln Ile Ser Gly Val Lys Arg Pro Leu Ser His Thr Asn Ser
145                 150                 155                 160

Phe Thr Gly Glu Arg Leu Pro Thr Phe Gly Val Glu Thr Pro Arg Glu
                165                 170                 175

Asn Glu Leu Gly Thr Leu Leu Gly Glu Leu Asp Thr Trp Gly Ile Gln
            180                 185                 190

Ile Phe Ser Ile Gly Glu Phe Ser Val Asn Arg Pro Leu Thr Cys Val
        195                 200                 205

Ala Tyr Thr Ile Phe Gln Ser Arg Glu Leu Leu Thr Ser Leu Met Ile
    210                 215                 220

Pro Pro Lys Thr Phe Leu Asn Phe Met Ser Thr Leu Glu Asp His Tyr
225                 230                 235                 240

Val Lys Asp Asn Pro Phe His Asn Ser Leu His Ala Ala Asp Val Thr
                245                 250                 255

Gln Ser Thr Asn Val Leu Leu Asn Thr Pro Ala Leu Glu Gly Val Phe
            260                 265                 270

Thr Pro Leu Glu Val Gly Gly Ala Leu Phe Ala Ala Cys Ile His Asp
        275                 280                 285

Val Asp His Pro Gly Leu Thr Asn Gln Phe Leu Val Asn Ser Ser Ser
    290                 295                 300

Glu Leu Ala Leu Met Tyr Asn Asp Glu Ser Val Leu Glu Asn His His
305                 310                 315                 320

Leu Ala Val Ala Phe Lys Leu Leu Gln Asn Gln Gly Cys Asp Ile Phe
                325                 330                 335

Cys Asn Met Gln Lys Lys Gln Arg Gln Thr Leu Arg Lys Met Val Ile
            340                 345                 350

Asp Ile Val Leu Ser Thr Asp Met Ser Lys His Met Ser Leu Leu Ala
        355                 360                 365

Asp Leu Lys Thr Met Val Glu Thr Lys Lys Val Ala Gly Ser Gly Val
    370                 375                 380

Leu Leu Leu Asp Asn Tyr Thr Asp Arg Ile Gln Val Leu Glu Asn Leu
385                 390                 395                 400

Val His Cys Ala Asp Leu Ser Asn Pro Thr Lys Pro Leu Pro Leu Tyr
                405                 410                 415

Lys Arg Trp Val Ala Leu Leu Met Glu Glu Phe Phe Leu Gln Gly Asp
            420                 425                 430

Lys Glu Arg Glu Ser Gly Met Asp Ile Ser Pro Met Cys Asp Arg His
        435                 440                 445

Asn Ala Thr Ile Glu Lys Ser Gln Val Gly Phe Ile Asp Tyr Ile Val
    450                 455                 460
```

```
His Pro Leu Trp Glu Thr Trp Ala Ser Leu Val His Pro Asp Ala Gln
465                 470                 475                 480

Asp Ile Leu Asp Thr Leu Glu Glu Asn Arg Asp Tyr Tyr Gln Ser Met
            485                 490                 495

Ile Pro Pro Ser Pro Pro Ser Gly Val Asp Glu Asn Pro Gln Glu
            500             505                 510

Asp Arg Ile Arg Phe Gln Val Thr Leu Glu Glu Ser Asp Gln Glu Asn
            515                 520                 525

Leu Ala Glu Leu Glu Glu Gly Asp Glu Ser Gly Gly Glu Thr Thr Thr
            530             535             540

Thr Gly Thr Thr Gly Thr Thr Ala Ala Ser Ala Leu Arg Ala Gly Gly
545                 550                 555                 560

Gly Gly Gly Gly Gly Gly Gly Met Ala Pro Arg Thr Gly Gly Cys Gln
                565             570                 575

Asn Gln Pro Gln His Gly Gly Met
            580
```

(2) INFORMATION FOR SEQ ID NO: 5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 5:

GGGTGACAGG GTTGATGCT                                  19

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 6:

TCGCTTAGTT TTACCGTTTT C                            21

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 7:

TATCGCCTCC ATCAACAAAC TT                         22

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 8:

GACACAGAAC AGCCACCTC                                  19

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 9:

```
AGCAAGTTCA GCCTGGTTAA G                                              21
```

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 10:

```
CTTATGAGTA TTTCTTCCAG GGTA                                           24
```

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 11:

```
ATCATGGTTA CAAATTATCG AAGCCAATTA                                     30
```

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

```
GCTCCTCCCT CATCTTCTTA                                                20
```

(2) INFORMATION FOR SEQ ID NO: 13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 13:

```
AGGACAGCCA AGTGATTT                                                  18
```

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 14:

```
TGCGCTGGCC TTCCTGGTAG                                                20
```

CYCLIC GMP PHOSPHODIESTERASE

This application is a divisional application of U.S. application Ser. No. 09/240,359 filed Jan. 29, 1999, issued on July 3, 2001, as U.S. Pat. No. 6,255,456, entitled CYCLIC GMP PHOSPHODIESTERASE, which is a divisional application of U.S. application Ser. No. 08/987,466 filed December 9, 1997, issued on July 13, 1999, as U.S. Pat. No. 5,922,595, entitled CYCLIC OMP PHOSPHODIBSTJ3RASE, the contents of all which are hereby incorporated by reference.

FIELD OF THE INVENTION

This invention relates to the nucleic acid and amino acid sequences of a cyclic GMP phosphodiesterase and to the use of these sequences in the diagnosis, prevention, and treatment of cancer and immune disorders.

BACKGROUND OF THE INVENTION

Cyclic nucleotides (cAMP and cGMP) function as intracellular second messengers to transduce a variety of extracellular signals, including hormones, light, and neurotransmitters. Cyclic nucleotide phosphodiesterases (PDEs) degrade cyclic nucleotides to the corresponding monophosphates, thereby regulating the intracellular concentrations of cyclic nucleotides and their effects on signal transduction. At least seven families of mammalian PDEs have been identified based on substrate specificity and affinity, sensitivity to cofactors, and sensitivity to inhibitory drugs (Beavo, J. A. (1995) Physiological Reviews 75:725–48). Several of these families contain distinct genes many of which are expressed in different tissues as splice variants. Within families, there are multiple isozymes and multiple splice variants of those isozymes. The existence of multiple PDE families, isozymes, and splice variants presents an opportunity for regulation of cyclic nucleotide levels and functions.

Type 1 PDEs (PDE1s) are $Ca^{2+}$/calmodulin dependent, appear to contain three different genes, each having at least two different splice variants. PDE1s have been found in the lung, heart, and brain. Some of the calmodulin-dependent PDEs are regulated in vitro by phosphorylation/dephosphorylation. Phosphorylation of PDE1 decreases the affinity of the enzyme for calmodulin as well as PDE activity, while increasing steady state levels of cAMP. PDE2s are cGMP stimulated PDEs that are localized in the brain that are thought to mediate the effects of cAMP on catecholamine secretion. PDE3s are one of the major families of PDEs present in vascular smooth muscle. PDE3s are inhibited by cGMP, have high specificity for cAMP as a substrate, and play a role in cardiac function. One isozyme of PDE3 is regulated by one or more insulin-dependent kinases. PDE4s are the predominant isoenzymes in most inflammatory cells, some PDE4s are activated by cAMP-dependent phosphorylation. PDE5s are thought to be cGMP specific, but may also affect cAMP function. High levels of PDE5s are found in most smooth muscle preparations, in platelets and in the kidney. PDE6s play a role in vision and are regulated by light and cGMP. The PDE7 class, consisting of only one known member, is cAMP specific and is most closely related to PDE4. PDE7 is not inhibited by rolipram, a specific inhibitor of PDE4 (See Beavo, supra). PDE8 represents a new family of PDEs that are cAMP specific, most closely related to PDE4, insensitive to rolipram, and sensitive to dipyridimole.

PDEs are composed of a catalytic domain of ~270 amino acids, an N-terminal regulatory domain responsible for binding cofactors, and, in some cases, a C-terminal domain of unknown function. A conserved motif, HDXXHXGXXN, has been identified in the catalytic domain of all PDEs. PDE families display approximately 30% amino acid identity within this catalytic domain, however isozymes within the same family typically display about 85–95% identity in this region (e.g. PDE4A vs PDE4B). Furthermore, within a family there is extensive similarity (>60%) outside the catalytic domain, while across families, there is little or no sequence similarity.

Many functions of immune and inflammatory responses are inhibited by agents that increase intracellular levels of cAMP (Verghese, M. W. et al. (1995) Mol. Pharmacol. 47:1164–1171). A variety of diseases have been attributed to increased PDE activity and associated with decreased levels of cyclic nucleotides. A form of diabetes insipidus in the mouse has been associated with increased PDE4 activity, and an increase in low-$K_m$ cAMP PDE activity has been reported in leukocytes of atopic patients. Defects in PDEs have also been associated with retinal disease. Retinal degeneration in the rd mouse, autosomal recessive retinitis pigmentosa in humans, and rod/cone dysplasia 1 in Irish Setter dogs have been attributed to mutations in the PDE6B gene. PDE3 has been associated with cardiac disease.

Many inhibitors of PDEs have been identified and have undergone clinical evaluation. PDE3 inhibitors are being developed as antithrombotic agents, antihypertensive agents, and as cardiotonic agents useful in the treatment of congestive heart failure. Rolipram, a PDE4 inhibitor, has been used in the treatment of depression, and other inhibitors of PDE4 are undergoing evaluation as anti-inflammatory agents. Rolipram has also been shown to inhibit lipopolysaccharide (LPS) induced TNF-alpha which has been shown to enhance HIV-1 replication in vitro. Therefore, rolipram may inhibit HIV-1 replication (Angel, J. B. et al. (1995) AIDS 9:1137–44). Additionally, rolipram, based on its ability to suppress the production of cytokines such as TNF alpha and beta and interferon gamma, has been shown to be effective in the treatment of encephalomyelitis. Rolipram may also be effective in treating tardive dyskinesia and was effective in treating multiple sclerosis in an experimental animal model (Sommer, N. et al. (1995) Nat. Med. 1:244–248; Sasaki, H. et al. (1995) Eur. J. Pharmacol 282:71–76).

Theophylline is a nonspecific PDE inhibitor used in the treatment of bronchial asthma and other respiratory diseases. Theophylline is believed to act on airway smooth muscle function and in an anti-inflammatory or immunomodulatory capacity in the treatment of respiratory diseases (Banner, K. H. and Page, C. P. (1995) Eur. Respir. J. 8:996–1000). Pentoxifylline is another nonspecific PDE inhibitor used in the treatment of intermittent claudication and diabetes-induced peripheral vascular disease. Pentoxifylline is also known to block TNF-alpha production and may inhibit HIV-1 replication (Angel et al., supra).

PDEs have also been reported to effect cellular proliferation of a variety of cell types and have been implicated in various cancers. Bang et al. (1994; Proc Natl Acad Sci USA 91:5330–5334) reported that growth of prostate carcinoma cell lines DU 145 and LNCaP was inhibited by delivery of cAMP derivatives and phosphodiesterase inhibitors. These cells also showed a permanent conversion in phenotype from epithelial to neuronal morphology. Others have suggested that PDE inhibitors have the potential to regulate mesangial cell proliferation and lymphocyte proliferation (Matousovic, K. et al. (1995) J. Clin. Invest. 96:401–410; Joulain, C. et al. (1995) J. Lipid Mediat. Cell Signal. 11:63–79, respectively). Finally, Deonarain et al. (1994; Br.

J. Cancer 70:786–94) describe a cancer treatment that involves intracellular delivery of phosphodiesterases to particular cellular compartments of tumors which results in cell death.

The discovery of new cyclic nucleotide phosphodiesterases and the polynucleotides encoding them satisfies a need in the art by providing new compositions which are useful in the diagnosis, prevention, and treatment of cancer and immune disorders.

SUMMARY OF THE INVENTION

The invention features a substantially purified polypeptide, cyclic GMP phosphodiesterase (PDE9A), comprising the amino acid sequence of SEQ ID NO:1 or a fragment of SEQ ID NO:1.

The invention further provides a substantially purified variant of PDE9A having at least 90% amino acid identity to the amino acid sequence of SEQ ID NO:1 or a fragment of SEQ ID NO:1. The invention also provides an isolated and purified polynucleotide sequence encoding the polypeptide comprising the amino acid sequence of SEQ ID NO:1 or a fragment of SEQ ID NO:1. The invention also includes an isolated and purified polynucleotide variant having at least 90% polynucleotide identity to the polynucleotide sequence encoding the polypeptide comprising the amino acid sequence of SEQ ID NO:1 or a fragment of SEQ ID NO:1.

Additionally, the invention provides a composition comprising a polynucleotide sequence encoding the polypeptide comprising the amino acid sequence of SEQ ID NO:1 or a fragment of SEQ ID NO:1. The invention further provides an isolated and purified polynucleotide sequence which hybridizes under stringent conditions to the polynucleotide sequence encoding the polypeptide comprising the amino acid sequence of SEQ ID NO:1 or a fragment of SEQ ID NO:1, as well as an isolated and purified polynucleotide sequence which is complementary to the polynucleotide sequence encoding the polypeptide comprising the amino acid sequence of SEQ ID NO:1 or a fragment of SEQ ID NO:1.

The invention also provides an isolated and purified polynucleotide sequence comprising SEQ ID NO:2 or a fragment of SEQ ID NO:2, and an isolated and purified polynucleotide variant having at least 90% polynucleotide identity to the polynucleotide sequence comprising SEQ ID NO:2 or a fragment of SEQ ID NO:2. The invention also provides an isolated and purified polynucleotide sequence which is complementary to the polynucleotide sequence comprising SEQ ID NO:2 or a fragment of SEQ ID NO:2.

The invention further provides an expression vector containing at least a fragment of the polynucleotide sequence encoding the polypeptide comprising the amino acid sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide sequence encoding PDE9A under conditions suitable for the expression of the polypeptide; and (b) recovering the polypeptide from the host cell culture.

The invention also provides a pharmaceutical composition comprising a substantially purified PDE9A having the amino acid sequence of SEQ ID NO:1 or a fragment of SEQ ID NO:1 in conjunction with a suitable pharmaceutical carrier.

The invention further includes a purified antibody which binds to a polypeptide comprising the amino acid sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of an antagonist of PDE9A.

The invention also provides a method for treating or preventing an immune disorder, the method comprising administering to a subject in need of such treatment an effective amount of an antagonist of PDE9A.

The invention also provides a method for detecting a polynucleotide encoding PDE9A in a biological sample containing nucleic acids, the method comprising the steps of: (a) hybridizing the complement of the polynucleotide sequence encoding the polypeptide comprising SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding PDE9A in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of PDE9A. The alignments were produced using MACDNASIS PRO software (Hitachi Software Engineering Co. Ltd. San Bruno, Calif.).

FIGS. 2A, 2B, 2C, and 2D, show the amino acid sequence alignments among PDE9A (828228; SEQ ID NO:1), PDE8A (SEQ ID NO:3), and a cAMP-specific PDE from *Drosophila melanogaster* (GI 829179; SEQ ID NO:4), produced using the multisequence alignment program of DNASTAR software (DNASTAR Inc, Madison Wis.).

DESCRIPTION OF THE INVENTION

Figure 3:
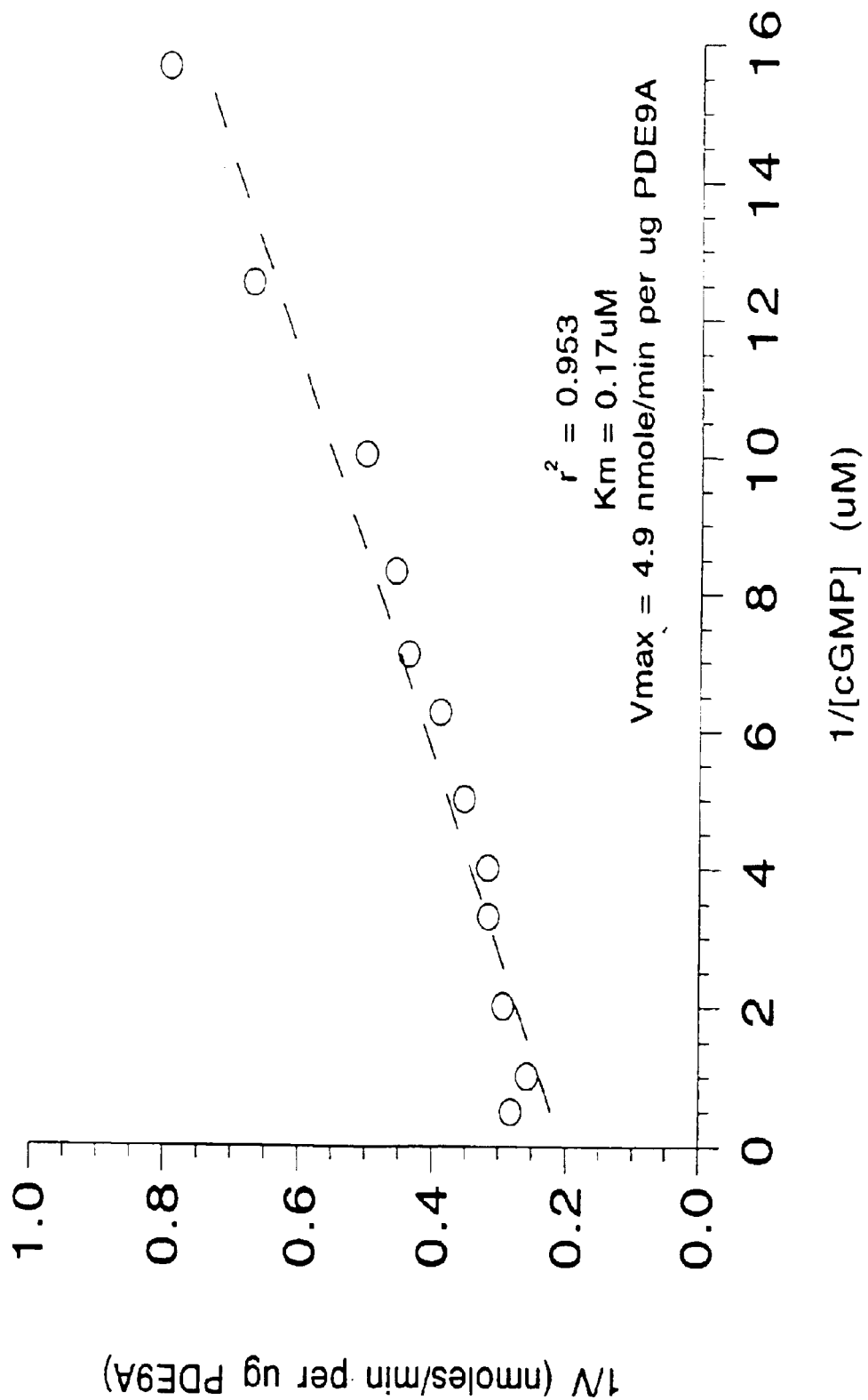
FIG. 3 shows the double-reciprocal, Lineweaver-Burke plot for the activity of PDE9A using cGMP as a substrate; the positive X axis reflects the reciprocal of the substrate (cGMP) concentration (1/S), and the positive Y axis reflects the reciprocal of the reaction velocity (1/V). Lineweaver-Burke analysis was performed according to Segal, I. H. (*Enzyme Kinetics* (1995) pp. 214–245, John Wiley and Sons, New York, N.Y.)

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein, and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

PDE9A, as used herein, refers to the amino acid sequences of substantially purified PDE9A obtained from any species, particularly mammalian, including bovine, ovine, porcine, murine, equine, and preferably human, from any source whether natural, synthetic, semi-synthetic, or recombinant.

The term "agonist," as used herein, refers to a molecule which, when bound to PDE9A, increases or prolongs the duration of the effect of PDE9A. Agonists may include proteins, nucleic acids, carbohydrates, or any other molecules which bind to and modulate the effect of PDE9A.

An "allele" or "allelic sequence," as used herein, is an alternative form of the gene encoding PDE9A. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding PDE9A as used herein, include those with deletions, insertions, or substitutions of different nucleotides resulting in a polynucleotide that encodes the same or a functionally equivalent PDE9A. Included within this definition are polymorphisms which may or may not be readily detectable using a particular oligonucleotide probe of the polynucleotide encoding PDE9A, and improper or unexpected hybridization to alleles, with a locus other than the normal chromosomal locus for the polynucleotide sequence encoding PDE9A. The encoded protein may also be "altered" and contain deletions, insertions, or substitutions of amino acid residues which produce a silent change and result in a functionally equivalent PDE9A. Deliberate amino acid substitutions may be made on the basis of similarity in polarity, charge, solubility, hydrophobicity, hydrophilicity, and/or the amphipathic nature of the residues as long as the biological or immunological activity of PDE9A is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence," as used herein, refers to an oligopeptide, peptide, polypeptide, or protein sequence, and fragment thereof, and to naturally occurring or synthetic molecules. Fragments of PDE9A are preferably about 5 to about 15 amino acids in length and retain the biological activity or the immunological activity of PDE9A. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification," as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist," as used herein, refers to a molecule which, when bound to PDE9A, decreases the amount or the duration of the effect of the biological or immunological activity of PDE9A. Antagonists may include proteins, nucleic acids, carbohydrates, antibodies or any other molecules which decrease the effect of PDE9A.

As used herein, the term "antibody" refers to intact molecules as well as fragments thereof, such as Fab, F(ab')$_2$, and Fv, which are capable of binding the epitopic determinant. Antibodies that bind PDE9A polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant," as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense," as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active," as used herein, refers to a protein having structural, regulatory, or biochemical functions of a naturally occurring molecule. Likewise, "immunologically active" refers to the capability of the natural, recombinant, or synthetic PDE9A, or any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by basepairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence," as used herein, refers broadly to any composition containing the given polynucleotide sequence. The composition may comprise a dry formulation or an aqueous solution. Compositions comprising polynucleotide sequences encoding PDE9A may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding PDE9A, by northern analysis is indicative of the presence of nucleic acids encoding PDE9A in a sample, and thereby correlates with expression of the transcript from the polynucleotide encoding PDE9A.

A "deletion," as used herein, refers to a change in the amino acid or nucleotide sequence and results in the absence of one or more amino acid residues or nucleotides.

The term "derivative," as used herein, refers to the chemical modification of a nucleic acid encoding or complementary to PDE9A or the encoded PDE9A. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody," as used herein, refers to antibody molecules in which amino acids have been replaced in the non-antigen binding regions in order to more closely resemble a human antibody, while still retaining the original binding ability.

The term "hybridization," as used herein, refers to any process by which a strand of nucleic acid binds with a complementary strand through base pairing.

The term "hybridization complex," as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as used herein, refers to a change in the activity of PDE9A. For example, modulation may cause an increase or a decrease in protein activity, binding characteristics, or any other biological, functional or immunological properties of PDE9A.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "sample," as used herein, is used in its broadest sense. A biological sample suspected of containing nucleic acid encoding PDE9A, or fragments thereof, or PDE9A itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding," as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "stringent conditions" refers to conditions which permit hybridization between polynucleotide sequences and the claimed polynucleotide sequences. Suitably stringent conditions can be defined by, for example, the concentrations of salt and/or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 µg/ml sheared and denatured salmon sperm DNA. Hybridization could occur under reduced stringency conditions as described above, but in 35% formamide or/and at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic or amino acid sequences that are removed from their natural environment, isolated or separated, and are at least 60% free, preferably 75% free, and most preferably 90% free from other components with which they are naturally associated.

A "substitution," as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of PDE9A, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

The Invention

The invention is based on the discovery of a new human cyclic-GMP specific phosphodiesterase (PDE9A), the polynucleotides encoding PDE9A, and the use of these compositions for the diagnosis, prevention, or treatment of cancer and immune disorders.

Nucleic acids encoding the PDE9A of the present invention were first identified in Incyte Clone 828228 from the prostate tissue cDNA library (PROSNOT06) using a computer search for amino acid sequence alignments. A consensus sequence, SEQ ID NO:2, was derived from extension of the nucleic acid sequence of this clone.

Figure 2A:
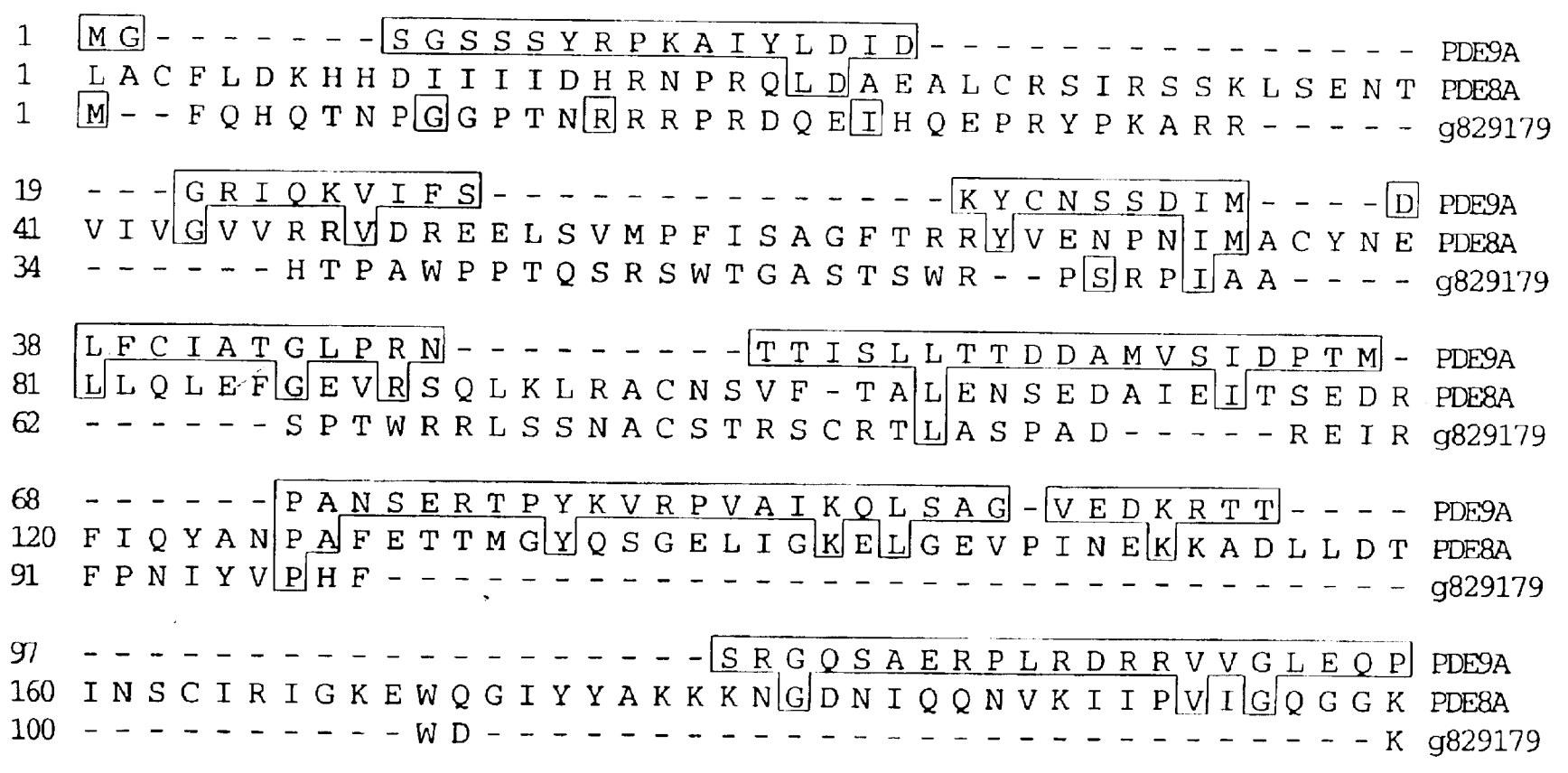

In one embodiment, the invention encompasses a polypeptide comprising the amino acid sequence of SEQ ID NO:1, as shown in FIGS. 1A, 1B, 1C, 1D, 1E, and 1F. PDE9A is 593 amino acids in length and has a consensus signature sequence for cyclic nucleotide PDEs at $H_{352}$DLDHPGYNN. This sequence is a part of one of two potential divalent cation binding sites conserved in PDEs, and having the general structure of HXXXH($X_{6-24}$)E. The first of these sites is found in the sequence $H_{312}$ - - - $H_{316}$ - - - $D_{341}$, and has $D_{341}$ as a conservative amino acid substitution for E. This substitution is found in at least one other PDE, PDE7. The second of these sites is found in the sequence $H_{352}$ - - - $H_{356}$ - - - $E_{382}$. As shown in FIGS. 2A, 2B, 2C, and 2, PDE9A has chemical and structural homology with PDE8A (SEQ ID NO:3) and the cAMP-specific PDE from *D. melanogaster* (GI 829179; SEQ ID NO:4). In particular, PDE9A shares 24% identity with PDE8A and 20% identity with *D. melanogaster* cAMP PDE. The ~270 amino acid catalytic domain found in all PDEs extends approximately between residues $F_{288}$ and $W_{544}$ for PDE9A, and is 34% identical to PDE8A and 30% identical to *D. melanogaster* PDE in this region. The three proteins share the two divalent cation binding sites and the consensus signature sequence, HDXXHXGXXN. PDE9A exhibits a similar degree of homology (28% to 32%) in the catalytic domain to other representatives of the PDE families 1, 2, 3, 4, 5, 6, and 7 (data not shown).

Figure 4:
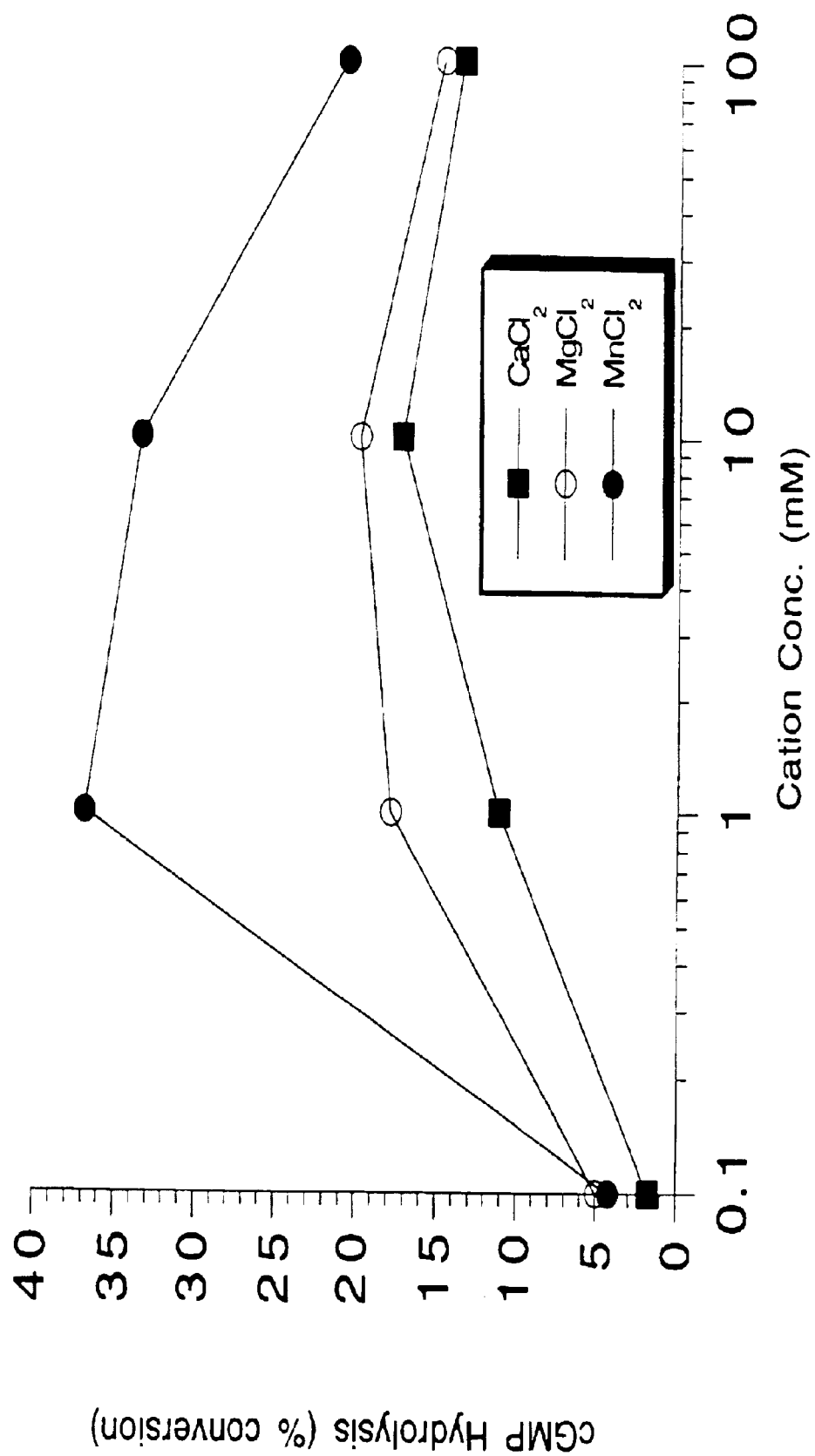
FIG. 4 shows the dependence of PDE9A activity on divalent cation concentration; the positive X axis reflects cation concentration (mM), and the positive Y axis reflects the percent hydrolysis of cAMP. Divalent cations tested were calcium chloride ($CaCL_2$; squares), magnesium chloride ($MgCl_2$; open circles), and manganese chloride ($MnCl_2$; closed circles).
Figure 5:
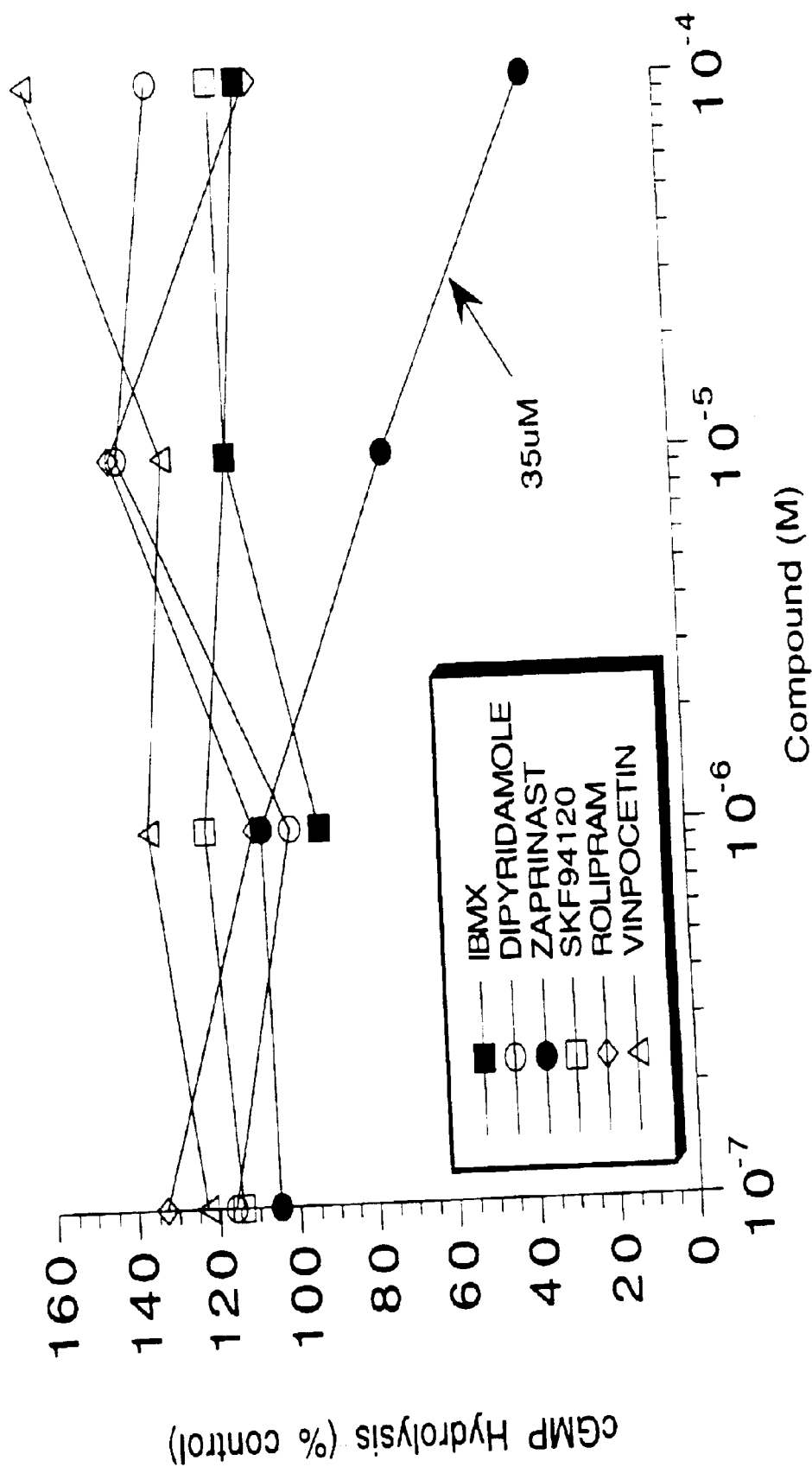
FIG. 5 shows the effect of various PDE inhibitors on the activity of PDE9A; the positive X axis reflects the concentration of inhibitor (M), and the positive Y axis reflects the percent hydrolysis of cGMP relative to an uninhibited control incubation (100%).

A 1.8 kb region of PDE9A encoding the full length of the protein was cloned into the baculovirus transfer vector pFASTBAC, expressed in sf9 cells, and a cell lysate prepared from these cells for enzyme assays. FIG. 3 shows the kinetics of enzyme activity of recombinant, purified PDE9A with cGMP as a substrate. PDE9A has a very high affinity for cGMP with a Km of 170 nM, and a very low affinity for cAMP (Km=230 υM, data not shown). FIG. 4 shows the dependence of PDE9A on divalent cations for maximal activity with a preference for $Mn^{++}$ over $Mg^{++}$ or $Ca^{++}$. The effects of various known PDE inhibitors on the activity of PDE9A are shown in FIG. 5. PDE9A was not inhibited by up to 100 μM of rolipram (inhibitor of PDE4), dipyridamole (inhibitor of PDE2, 4, 5, and 6), SKF94120 (inhibitor of PDE3), vinpocetine (inhibitor of PDE1), or IBMX (non-specific PDE inhibitor). PDE9A was inhibited by zaprinast (inhibitor of PDE5 and 6) with an $IC_{50}$ of 35 μM. Membrane-based northern analysis shows the expression of this sequence in various tissues, with the most significant expression in testis, ovary, small intestine, and colon. Electronic northern analysis using the LIFESEQ database further shows the expression of this sequence in various tissues, at least 50% of which are cancerous and at least 25% of which involves inflammation or the immune response. Of particular note is the expression of PDE9A in Crohn's disease.

The degree of similarity exhibited between the PDE9A and representatives of the other eight families of PDEs (28% to 30%) is consistent with that demonstrated between different PDE families (~30%). PDE9A is further distinguished from other known families by its specificity for cGMP and pattern of inhibition by known PDE inhibitors. PDE9A therefore appears to be a member of a new family of cyclic nucleotide phosphodiesterases designated PDE9.

The invention also encompasses PDE9A variants. A preferred PDE9A variant is one which has at least about 80%, more preferably at least about 90%, and most preferably at least about 95% amino acid sequence identity to the PDE9A amino acid sequence, and which contains at least one functional or structural characteristic of PDE9A.

The invention also encompasses polynucleotides which encode PDE9A. In a particular embodiment, the invention encompasses a polynucleotide sequence comprising the sequence of SEQ ID NO:2, which encodes a PDE9A.

The invention also encompasses a variant of a polynucleotide sequence encoding PDE9A. In particular, such a variant polynucleotide sequence will have at least about 80%, more preferably at least about 90%, and most preferably at least about 95% polynucleotide sequence identity to the polynucleotide sequence encoding PDE9A. A particular aspect of the invention encompasses a variant of SEQ ID NO:2 which has at least about 80%, more preferably at least about 90%, and most preferably at least about 95% polynucleotide sequence identity to SEQ ID NO:2.

It will be appreciated by those skilled in the art that as a result of the degeneracy of the genetic code, a multitude of nucleotide sequences encoding PDE9A, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring PDE9A, and all such variations are to be considered as being specifically disclosed.

Although nucleotide sequences which encode PDE9A and its variants are preferably capable of hybridizing to the nucleotide sequence of the naturally occurring PDE9A under appropriately selected conditions of stringency, it may be advantageous to produce nucleotide sequences encoding PDE9A or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PDE9A and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode PDE9A and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding PDE9A or any fragment thereof.

Also encompassed by the invention are polynucleotide sequences that are capable of hybridizing to the claimed nucleotide sequences, and in particular, those shown in SEQ ID NO:2, or a fragment of SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by GIBCO/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding PDE9A may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTER FINDER libraries to walk genomic DNA (Clontech, Palo Alto, Calif.). This process avoids the need to screen libraries and is useful in finding intron/exon junctions. When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode PDE9A may be used in recombinant DNA molecules to direct expression of PDE9A, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express PDE9A.

As will be understood by those of skill in the art, it may be advantageous to produce PDE9A-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter PDE9A encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding PDE9A may be ligated to a heterologous sequence to encode a fusion protein. For example, to screen peptide libraries for inhibitors of PDE9A activity, it may be useful to encode a chimeric PDE9A protein that can be recognized by a commercially available antibody. A fusion protein may also be engineered to contain a cleavage site located between the PDE9A encoding sequence and the heterologous protein sequence, so that PDE9A may be cleaved and purified away from the heterologous moiety.

In another embodiment, sequences encoding PDE9A may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of PDE9A, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of PDE9A, or any part thereof, may be altered during direct synthesis and/or combined using chemical methods with sequences from other proteins, or any part thereof, to produce a variant polypeptide.

In order to express a biologically active PDE9A, the nucleotide sequences encoding PDE9A or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding PDE9A and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding PDE9A. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector-enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (GIBCO/BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding PDE9A, vectors based on SV40 or EBV may be used with an appropriate selectable marker.

In bacterial systems, a number of expression vectors may be selected depending upon the use intended for PDE9A. For example, when large quantities of PDE9A are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding PDE9A may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding PDE9A may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express PDE9A. For example, a 1.8 kb region of PDE9A encoding the full length protein was PCR-amplified and cloned into the baculovirus transfer vector pFASTBAC (Life Technologies, Inc., Gaithersburg, Md.), which had been modified to include a 5' FLAG tag. Recombinant virus stocks were prepared according to the manufacturer's protocol. Sf9 cells were cultured in Sf900 II Sfm serum free media (Life Technologies Inc.) at 27° C. For expression, $1 \times 10^8$ Sf9 cells were infected at a multiplicity of infection of 5 in a final volume of 50 mls. Three days post-infection, the cells were harvested and enzyme-containing lysates were prepared. To monitor expression, 1 μl each of mock-infected and PDE9A-infected cell lysate was electrophoresed in a polyacrylamide gel and either silver-stained by standard methods or transferred to nitrocellulose and Western blotted with an anti-FLAG antibody (M2, Scientific Imaging System, Eastman Kodak, New Haven, Conn.) at a concentration of 2 mg/ml.

In mammalian host cells, a number of viral-based expression systems may be utilized. In cases where an adenovirus is used as an expression vector, sequences encoding PDE9A may be ligated into an adenovirus transcription/translation complex consisting of the late promoter and tripartite leader sequence. Insertion in a non-essential E1 or E3 region of the viral genome may be used to obtain a viable virus which is capable of expressing PDE9A in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding PDE9A. Such signals include the ATG initiation codon and adjacent sequences. In cases where sequences encoding PDE9A, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express PDE9A may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding PDE9A is inserted within a marker gene sequence, transformed cells containing sequences encoding PDE9A can be identified by the absence of marker gene function. Alternatively, a marker gene can be placed in tandem with a sequence encoding PDE9A under the control of a single promoter. Expression of the marker gene in response to induction or selection usually indicates expression of the tandem gene as well.

Alternatively, host cells which contain the nucleic acid sequence encoding PDE9A and express PDE9A may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding PDE9A can be detected by DNA-DNA or DNA-RNA hybridization or amplification using probes or fragments or fragments of polynucleotides encoding PDE9A. Nucleic acid amplification based assays involve the use of oligonucleotides or oligomers based on the sequences encoding PDE9A to detect transformants containing DNA or RNA encoding PDE9A.

A variety of protocols for detecting and measuring the expression of PDE9A, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on PDE9A is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding PDE9A include oligolabeling, nick translation, end-labeling or PCR amplification using a labeled nucleotide. Alternatively, the sequences encoding PDE9A, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison, Wis.); and U.S. Biochemical Corp., (Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding PDE9A may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode PDE9A may be designed to contain signal sequences which direct secretion of PDE9A through a prokaryotic or eukaryotic cell membrane. Other constructions may be used to join sequences encoding PDE9A to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and PDE9A may be used to facilitate purification. One such expression vector provides for expression of a fusion protein containing PDE9A and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3:263–281) while the enterokinase cleavage site provides a means for purifying PDE9A from the fusion protein. A discussion of vectors which contain fusion proteins is provided in Kroll, D. J. et al. (1993; DNA Cell Biol. 12:441–453).

In addition to recombinant production, fragments of PDE9A may be produced by direct peptide synthesis using solid-phase techniques (Merrifield, J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of PDE9A may be chemically synthesized separately and combined using chemical methods to produce the full length molecule.

Therapeutics

Chemical and structural homology exists among PDE9A, and PDE8A, and *D. melanogaster* cAMP PDE. In addition, PDE9A is expressed in cancer and tissues associated with inflammation and the immune response. Therefore, PDE9A appears to play a role in cancer and immune disorders. In particular, inhibitors of PDE have been shown to be effective in the treatment of these types of diseases and disorders.

Therefore, in one embodiment, an antagonist of PDE9A may be administered to a subject to prevent or treat a cancer. Such cancers may be, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds PDE9A may be used directly as an antagonist or indirectly as a targeting or delivery mechanism for bringing a pharmaceutical agent to cells or tissue which express PDE9A.

In another embodiment, a vector expressing the complement of the polynucleotide encoding PDE9A may be administered to a subject to treat or prevent a cancer including, but not limited to, the types of cancer described above.

In another embodiment, an antagonist of PDE9A may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections; and trauma.

In another embodiment, a vector expressing the complement of the polynucleotide encoding PDE9A may be administered to a subject to treat or prevent an immune disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PDE9A may be produced using methods which are generally known in the art. In particular, purified PDE9A may be used to produce antibodies or to screen libraries of pharmaceutical agents to identify those which specifically bind PDE9A.

Antibodies to PDE9A may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with PDE9A or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PDE9A have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of PDE9A amino acids may be fused with those of another protein such as keyhole limpet hemocyanin and antibody produced against the chimeric molecule.

Monoclonal antibodies to PDE9A may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce PDE9A-specific single chain antibodies. Antibodies with related specificity, but of distinct idiotypic composition, may be generated by chain shuffling from random combinatorial immunoglobulin libraries (Burton, D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for PDE9A may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PDE9A and its specific antibody. A two-site, monoclonal-based immunoassay utilizing monoclonal antibodies reactive to two non-interfering PDE9A epitopes is preferred, but a competitive binding assay may also be employed (Maddox, supra).

In another embodiment of the invention, the polynucleotides encoding PDE9A, or any fragment or complement thereof, may be used for therapeutic purposes. In one aspect, the complement of the polynucleotide encoding PDE9A may be used in situations in which it would be desirable to block the transcription of the mRNA. In particular, cells may be transformed with sequences complementary to polynucleotides encoding PDE9A. Thus, complementary molecules or fragments may be used to modulate PDE9A activity, or to achieve regulation of gene function. Such technology is now well known in the art, and sense or antisense oligonucleotides or larger fragments, can be designed from various locations along the coding or control regions of sequences encoding PDE9A.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding PDE9A. These techniques are described both in Sambrook et al. (supra) and in Ausubel et al. (supra).

Genes encoding PDE9A can be turned off by transforming a cell or tissue with expression vectors which express high levels of a polynucleotide or fragment thereof which encodes PDE9A. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding PDE9A (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding PDE9A.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PDE9A. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of PDE9A, antibodies to PDE9A, mimetics, agonists, antagonists, or inhibitors of PDE9A. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of PDE9A, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example PDE9A or fragments thereof, antibodies of PDE9A, agonists, antagonists or inhibitors of PDE9A, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind PDE9A may be used for the diagnosis of conditions or diseases characterized by expression of PDE9A, or in assays to monitor patients being treated with PDE9A, agonists, antagonists or inhibitors. The antibodies useful for diagnostic purposes may be prepared in the same manner as those described above for therapeutics. Diagnostic assays for PDE9A include methods which utilize the antibody and a label to detect PDE9A in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring PDE9A are known in the art and provide a basis for diagnosing altered or abnormal levels of PDE9A expression. Normal or standard values for PDE9A expression are established by combining body fluids or cell extracts taken from normal mammalian subjects, preferably human, with antibody to PDE9A under conditions suitable for complex formation. The amount of standard complex formation may be quantified by various methods, but preferably by photometric means. Quantities of PDE9A expressed in subject, control, and disease, samples from biopsied tissues are compared with the standard values. Deviation between standard and subject values establishes the parameters for diagnosing disease.

In another embodiment of the invention, the polynucleotides encoding PDE9A may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PDE9A may be correlated with disease. The diagnostic assay may be used to distinguish between absence, presence, and excess expression of PDE9A, and to monitor regulation of PDE9A levels during therapeutic intervention.

In one aspect, hybridization with PCR probes which are capable of detecting polynucleotide sequences, including genomic sequences, encoding PDE9A or closely related molecules, may be used to identify nucleic acid sequences which encode PDE9A. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding PDE9A, alleles, or related sequences.

Probes may also be used for the detection of related sequences, and should preferably contain at least 50% of the nucleotides from any of the PDE9A encoding sequences. The hybridization probes of the subject invention may be DNA or RNA and derived from the nucleotide sequence of SEQ ID NO:2 or from genomic sequence including promoter, enhancer elements, and introns of the naturally occurring PDE9A.

Means for producing specific hybridization probes for DNAs encoding PDE9A include the cloning of nucleic acid sequences encoding PDE9A or PDE9A derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding PDE9A may be used for the diagnosis of conditions or disorders which are associated with expression of PDE9A. Examples of such conditions or disorders include, but are not limited to, cancers, such as adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders, such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections; and trauma. The polynucleotide sequences encoding PDE9A may be used in Southern or northern analysis, dot blot, or other membrane-based technologies; in PCR technologies; or in dipstick, pin, ELISA assays or microarrays utilizing fluids or tissues from patient biopsies to detect altered PDE9A expression. Such qualitative or quantitative methods are well known in the art.

In a particular aspect, the nucleotide sequences encoding PDE9A may be useful in assays that detect activation or induction of various cancers, particularly those mentioned above. The nucleotide sequences encoding PDE9A may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding PDE9A in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of PDE9A, a normal or standard profile for expression is established. This may be accomplished by combining body fluids or cell extracts taken from normal subjects, either animal or human, with a sequence, or a fragment thereof, which encodes PDE9A, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once the presence of a disorder is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PDE9A may involve the use of PCR. Such oligomers may be chemically synthesized, generated enzymatically, or produced in vitro. Oligomers will preferably consist of two nucleotide sequences, one with sense orientation (5→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of PDE9A include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of disease, to diagnose disease, and to develop and monitor the activities of therapeutic agents.

In one embodiment, the microarray is prepared and used according to the methods known in the art such as those described in PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619).

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably about 15 to 30 nucleotides in length, and most preferably about 20 to 25 nucleotides in length. For a certain type of microarray, it may be preferable to use oligonucleotides which are only 7 to 10 nucleotides in length. The microarray may contain oligonucleotides which cover the known 5' (or 3') sequence, or may contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from 2 to 1,000,000.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon or any other type of membrane, filter, chip, glass slide, or any other suitable solid support.

In one aspect, the oligonucleotides may be synthesized on the surface of the substrate by using a chemical coupling procedure and an ink jet application apparatus, such as that described in PCT application WO95/251116 (Baldeschweiler et al.). In another aspect, a "gridded" array analogous to a dot or slot blot (HYBRIDOT apparatus, GIBCO/BRL) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including BRINKMANN multichannel pipettors or robotic instruments) and may contain 8, 24, 96, 384, 1536 or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TransProbe kits (Pharmacia) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. A detection system may be used to measure the absence, presence, and amount of hybridization for all of the distinct sequences simultaneously. This data may be used for large scale correlation studies or functional analysis of the sequences, mutations, variants, or polymorphisms among samples (Heller, R. A. et al., (1997) Proc. Natl. Acad. Sci. 94:2150–55).

In another embodiment of the invention, the nucleic acid sequences which encode PDE9A may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding PDE9A on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, PDE9A, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between PDE9A and the agent being tested, may be measured.

Another technique for drug screening which may be used provides for high throughput screening of compounds having suitable binding affinity to the protein of interest as described in published PCT application WO84/03564. In this method, as applied to PDE9A large numbers of different small test compounds are synthesized on a solid substrate, such as plastic pins or some other surface. The test compounds are reacted with PDE9A, or fragments thereof, and washed. Bound PDE9A is then detected by methods well known in the art. Purified PDE9A can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PDE9A specifically compete with a test compound for binding PDE9A. In this manner, the antibodies can be used to detect the presence of any peptide which shares one or more antigenic determinants with PDE9A.

In additional embodiments, the nucleotide sequences which encode PDE9A may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I PROSNOT06 cDNA Library Construction

The PROSNOT06 cDNA library was constructed from microscopically normal prostate tissue obtained from a 57-year-old Causcasian male. This tissue was associated with cDNA library PROSTUT04, a prostate tumor from the same patient. Both tissues were excised when the patient during a radical prostatectomy which included removal of both testes and excision of regional lymph nodes. Pathology indicated adenofibromatous hyperplasia and adenocarcinoma (Gleason grade 3+3) in both the right and left periphery of the prostate. There was perineural invasion, and the tumor perforated the capsule. The patient history reported a benign neoplasm of the large bowel. The patient was taking insulin for type I diabetes. The patient's family history included a malignant neoplasm of the prostate in the father and type I diabetes without complications in the mother.

The frozen tissue was homogenized and lysed using a Brinkman Homogenizer Polytron-PT 3000 (Brinkman Instruments, Inc. Westbury, N.Y.) in guanidinium isothiocyanate solution. 1.0 ml of 2M sodium acetate was added to the lysate and the lysate was extracted once with phenol chloroform at pH 5.5 per Stratagene's RNA isolation protocol (Stratagene), and once with acid phenol at pH 4.7. The RNA was precipitated with an equal volume of isopropanol according to Stratagene's protocol. RNA pellet was resuspended in DEPC-treated water and treated with DNase for 50 min at 37 C. The reaction was stopped with an equal volume of acid phenol, and the RNA was precipitated using 0.3 M sodium acetate and 2.5 volumes of ethanol and resuspended in DEPC-treated water. The RNA was isolated with the OLIGOTEX kit (QIAGEN Inc, Chatsworth, Calif.) and used to construct the cDNA library.

The mRNA was handled according to the recommended protocols in the SUPERSCRIPT Plasmid System for cDNA synthesis and plasmid cloning (Cat. #18248–013; GIBCO/BRL, Gaithersburg, Md.). cDNAs were fractionated on a SEPHAROSE CL4B colmn (Cat. 275105, Pharmacia), and those cDNAs exceeding 400 bp were ligated into PSPORT1. The plasmid PSPORT1 was subsequently transformed into DH5α competent cells (Cat. #18258–012, GIBCO/BRL).

II Isolation and Sequencing of cDNA Clones

Plasmid DNA was released from the cells and purified using the REAL Prep 96 Plasmid Kit (Catalog #26173, QIAGEN). This kit enabled the simultaneous purification of 96 samples in a 96-well block using multi-channel reagent dispensers. The recommended protocol was employed with the following modifications: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441 f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S. F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Human multiple tissue northern blots (Clontech, Palo Alto, Calif.) were hybridized with a probe consisting of the 5' most 1090 nucleotides of clone 828228. Probe DNA was labeled with $^{32}$P using the "Ready-To-Go" random prime labeling kit (Pharmacia Biotech Inc., Piscataway, N.J.) and washed to a stringency of 0.5×SSC, 65° C. The highest levels of PDE9A were seen in spleen, small intestine, and brain, but detectable levels were seen in all tissues examined.

Computer techniques analogous to membrane based northern analysis were also performed using BLAST (Altschul (1993), supra; Altschul (1990), supra). The basis of the search is the product score which is defined as:

% sequence identity×% maximum BLAST score/100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding PDE9A occurs. Abundance and percent abundance are also reported. Abundance directly reflects the number of times a particular transcript is represented in a cDNA library, and percent abundance is abundance divided by the total number of sequences examined in the cDNA library.

V Extension of PDE9A Encoding Polynucleotides cDNA sequences were extended by PCR amplification using human λgt10 testis or stomach cDNA libraries (Clontech Laboratories, Inc. Palo Alto, Calif.) and nested primers. For each reaction, $2.5 \times 10^7$ pfu were boiled for 5 minutes to release DNA. First round PCR (15 cycles) was performed with a PDE9A specific primer (9A specific-outer: 5'-GGGTGACAGGGTTGATGCT-3'; SEQ ID NO:5) and either a λgt10 forward (5'-TCGCTTAGTTTTACCGTTTTC-3' (SEQ ID NO:6), or a λgt10 reverse (5'-TATCGCCTCCATCAACAAACTT-3'; SEQ ID NO:7) primer. An aliquot, ⅟₅₀ of the reaction mixture, was used as a template for a second round of amplification (30 cycles) with a PDE9A specific primer (9A specific-inner: 5'-GACACAGAACAGCCACCTC-3'; SEQ ID NO:8) with either a nested λgt10 forward (5'-AGCAAGTTCAGCCTGGTTAAG-3'; SEQ ID NO:9) or λgt10 reverse (5'-CTTATGAGTATTTCTTCCAGGGTA-3'; SEQ ID NO:10) primer. Southern analysis of the PCR products used an internal PDE9A hybridization probe (5'-ATCATGGTTACAAATTATCGAAGCCAATTA-3'; SEQ ID NO:11). 5' RACE amplification was also performed on human brain mRNA (Clontech) to extend the sequence. 5' RACE was performed using a "5' RACE System for Rapid Amplification of cDNA Ends" kit (Life Technologies, Inc., Grand Island, N.Y.) according to the manufacturer's protocol. PDE9A specific primers used in the 5' RACE were: Reverse Transcriptase primer, 5'-GCTCCTCCCTCATCTTCTTA-3' (SEQ ID NO:12); Outer primer, 5'-AGGACAGCCAAGTGATTT-3' (SEQ ID NO:13); Inner primer, 5'-TGCGCTGGCCTTCCTGGTAG-3' (SEQ ID NO:14). Positive bands were subcloned and sequenced. All sequences subsequently incorporated into the extended PDE9A sequence were verified by sequencing multiple independent PCR amplifications from the cDNA library DNA using unique primers or by independent amplification from mRNA.

VI Labeling and Use of Individual Hybridization Probes

Hybridization probes derived from polynucleotide sequences of the invention are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, XbaI, or Pvu II; DuPont NEN).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots in a PHOSPHOIMAGER cassette (Molecular Dynamics, Sunnyvale, Calif.) for several hours, hybridization patterns are compared visually.

VII Microarrays

To produce oligonucleotides for a microarray, one of the nucleotide sequences of the present invention is examined using a computer algorithm which starts at the 3' end of the nucleotide sequence. The algorithm identified oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20 mers are synthesized and arranged on the surface of the silicon chip using a light-directed chemical process, such as that discussed in Chee, supra.

In the alternative, a chemical coupling procedure and an ink jet device are used to synthesize oligomers on the surface of a substrate (cf. Baldeschweiler, supra). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned image is examined to determine degree of complementarity and the relative abundance/expression level of each oligonucleotide sequence in the microarray.

VIII Complementary Polynucleotides

Sequences complementary to the PDE9A-encoding sequence, or any part thereof, are used to decrease or inhibit expression of naturally occurring PDE9A. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of PDE9A. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PDE9A-encoding transcript.

IX Expression of PDE9A

A 1.8 kb region of PDE9A encoding the full length protein (nucleotides 61–1842) was amplified and cloned into the baculovirus transfer vector PFASTBAC (Life Technologies, Inc., Gaithersburg, Md.), which had been modified to include a 5' FLAG tag. Recombinant virus stocks were prepared according to the manufacturer's protocol. Sf9 cells were cultured in Sf900 II Sfm serum free media (Life Technologies Inc.) at 27° C. For expression, $1 \times 10^8$ Sf9 cells were infected at a multiplicity of infection of 5 in a final volume of 50 mls. At three days post-infection, the cells were harvested, and enzyme-containing lysates were prepared as detailed below. To monitor expression, 1 ml each of mock-infected and PDE9A infected cell lysate was electrophoresed in a polyacrylamide gel and either silver-stained by standard methods or transferred to nitrocellulose and assayed using western analysis and an anti-FLAG antibody (M2, Scientific Imaging System, Eastman Kodak, New Haven, Conn.) at a concentration of 2 mg/ml. The secondary antibody was an alkaline phosphatase conjugated anitmouse IgG (Boehringer Mannheim, Indianapolis, Ind.) and the blot was visualized with a "BCIP/NBT phosphatase substrate system" (Kirkegaard & Perry Laboratories, Gaithersburg, Md.) according to the manufactur's protocol.

PDE9A to be used for assay was prepared from transfected Sf9 cells. Cells were harvested by centrifugation, resuspended in homogenization buffer (20 mM Tris-HCl, 2 mM benzamidine, 1 mM EDTA, 0.25 M sucrose, 100 uM PMSF, pH 7.5 ) at $1 \times 10^7$ cells/ml, and disrupted using a Branson sonicating probe (3x10 second pulses). Cellular debris was removed by centrifugation at 14,000xg for 10 minutes. The supernatant was stored at –70° C.

X Demonstration of PDE9A Activity

PDE activity was assayed by measuring the conversion of $^3$H-cGMP to $^3$H-guanosine in the presence of PDE9A and 5' nucleotidase. A one-step assay was run using a 100 uL assay containing 50 mM Tris-HCl pH 7.5, 10 mM $MgCl_2$, 0.1 unit 5' nucleotidase (from *Crotalus atrox* venom), and 0.0064–2.0 uM $^3$H-cGMP. The reaction was started by the addition of 25 μl of diluted enzyme supernatant. Reactions were run directly in mini Poly-Q scintillation vials (Beckman Instruments Inc., Fullerton Calif.). Assays were incubated at 37° C. for a time period that would yield less than 15% cGMP hydrolysis in order to avoid non-linearity associated with product inhibition. The reaction was stopped by the addition of 1 ml of Dowex AG1x8 (Cl form) resin (1:3 slurry). Three ml of scintillation fluid were added, and the vials were mixed. The resin in the vials was allowed to settle for 1 hr before counting. Soluble radioactivity associated with $^3$H-guanosine was quantitated using a Beta scintillation counter. The amount of radioactivity recovered is proportional to the activity of PDE9A in the reaction.

XI Production of PDE9A Specific Antibodies

PDE9A that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using LASERGENE software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring PDE9A Using Specific Antibodies

Naturally occurring or recombinant PDE9A is substantially purified by immunoaffinity chromatography using antibodies specific for PDE9A. An immunoaffinity column is constructed by covalently coupling PDE9A antibody to an activated chromatographic resin, such as CNBr-activated SEPHAROSE (Pharmacia & Upjohn). After the coupling, the resin is blocked and washed according to the manufacturer's instructions.

Media containing PDE9A is passed over the immunoaffinity column, and the column is washed under conditions that allow the preferential absorbance of PDE9A (e.g., high ionic strength buffers in the presence of detergent). The column is eluted under conditions that disrupt antibody/PDE9A binding (eg, a buffer of pH 2–3 or a high concentration of a chaotrope, such as urea or thiocyanate ion), and PDE9A is collected.

XIII Identification of Molecules Which Interact with PDE9A

PDE9A or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled PDE9A, washed and any wells with labeled PDE9A complex are assayed. Data obtained using different concentrations of PDE9A are used to calculate values for the number, affinity, and association of PDE9A with the candidate molecules.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polynucleotide encoding a polypeptide selected from the group consisting of:
   a) a polypeptide comprising the amino acid sequence of SEQ ID NO:1,
   b) a polypeptide comprising an amino acid sequence at least 90% identical to the amino acid sequence of SEQ ID NO:1,
   c) a fragment of a polypeptide having the amino acid sequence of SEQ 1) NO:1, said fragment having cyclic nucleotide phosphodiesterase activity, and
   d) an immunogenic fragment of a polypeptide of at least 5 amino acids of the amino acid sequence of SEQ ID NO:1, said immunogenic fragment is used to make an antibody which specifically binds to an isolated polypeptide selected from the group consisting of a), b) and c).

2. A recombinant polynucleotide comprising a promoter sequence operably linked to a polynucleotide of claim 1.

3. A cell transformed with a recombinant polynucleotide of claim 2.

4. A method for producing a polypeptide encoded by the polynucleotide of claim 1, the method comprising:
   a) culturing a cell under conditions suitable for expression of the polypeptide, wherein said cell is transformed with a recombinant polynucleotide, and said recombinant polynucleotide comprises a promoter sequence operably linked to a polynucleotide of claim 1, and
   b) recovering the polypeptide so expressed.

5. A method of claim 4, wherein the polypeptide comprises the amino acid sequence of SEQ ID NO:1.

6. An isolated polynucleotide selected from the group consisting of:
   a) a polynucleotide comprising the polynucleotide sequence of SEQ II) NQ:2,
   b) a polynucleotide comprising a polynucleotide sequence at least 90% identical to the polynucleotide sequence of SEQ ID NO:2,
   c) a polynucleotide complementary to a polynucleotide of a),
   d) a polynucleotide complemeiltary to a polynucleotide of b) and
   e) an RNA equivalent of a)–d).

7. A method for detecting a target polynucleotide in a sample, said target polynucleotide having a sequence of a polynucleotide of claim 6, the method comprising:
   a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and
   b) detecting the presence or absence of said hybridization complex, and, optionally, if present, the amount thereof.

8. A method of claim 7, wherein the probe comprises at least 60 contiguous nucleotides.

9. A method for detecting a target polynucleotide sample, said target polynucleotide having a sequence of a polynucleotide of claim 6, the method comprising:
   a) amplifying said target polynucleotide or fragment thereof using polymerase chain reaction amplification, and
   b) detecting the presence or absence of said amplified target polynucleotide or fragment thereof, and, optionally, if present, the amount thereof.

10. A method for assessing toxicity of a test compound, said method comprising:
    a) treating a biological sample containing nucleic acids with the test compound;
    b) hybridizing the nucleic acids of the treated biological sample with a probe comprising at least 20 contiguous nucleotides of a polynucleotide of claim 6 under conditions whereby a specific hybridization complex is formed between said probe and a target polynucleotide in the biological sample, said target polynucleotide comprising a polynucleotide sequence of a polynucleotide of claim 6 or fragment thereof;
    c) quantifying the amount of hybridization complex; and
    d) comparing the amount of hybridization complex in the treated biological sample with the amount of hybridization complex in an untreated biological sample, wherein a difference in the amount of hybridization complex in the treated biological sample is indicative of toxicity of the test compound.

11. A polynucleotide of claim 6, comprising the polynucleotide sequence of SEQ ID NO:2.

12. A method for screening a compound for effectiveness in altering expression of a target polynucleotide, wherein said target polynucleotide comprises a polynucleotide sequence of claim 11, the method comprising:
    a) exposing a sample comprising the target polynucleotide to a compound, under conditions suitable for the expression of the target polynucleotide,
    b) detecting altered expression of the target polynucleotide, and
    c) comparing the expression of the target polynucleotide in the presence of varying amounts of the compound and in the absence of the compound.

* * * * *